United States Patent [19]

Ting et al.

[11] Patent Number: 5,538,986

[45] Date of Patent: Jul. 23, 1996

[54] TRICYCLIC DERIVATIVES, COMPOSITIONS AND METHODS OF USE

[75] Inventors: Pauline C. Ting, New Providence; Daniel M. Solomon, Edison; Richard J. Friary, Bridgewater; Frank J. Villani, Fairfield; John J. Piwinski, Parsippany, all of N.J.; Joe F. Lee, Brooklyn, N.Y.; Dhiru B. Vashi, Princeton Junction, N.J.

[73] Assignee: Schering Corporation, Kenilworth, N.J.

[21] Appl. No.: 162,744

[22] Filed: Dec. 6, 1993

[51] Int. Cl.$^6$ .................. C07D 313/00; C07C 233/00; C07C 211/00; A61K 31/44; A61K 31/35; A61K 31/138; A61K 31/41

[52] U.S. Cl. .......... 514/337; 564/185; 564/215; 564/253; 564/337; 564/338; 564/342; 564/355; 564/360; 564/374; 564/380; 564/427; 558/61; 514/454; 514/510; 514/564; 514/617; 514/625; 514/649; 514/653; 514/654; 514/656; 546/270; 546/285; 549/354; 560/28; 560/36; 562/443; 562/444; 562/449; 562/450; 562/466; 562/492

[58] Field of Search .................. 549/354; 558/61; 564/185, 215, 253, 338, 337, 342, 355, 360, 379, 380, 427; 560/28, 36; 562/443, 444, 449, 450, 466, 492; 546/270, 285; 514/337, 454, 510, 509, 617, 625, 649, 653, 654, 650

[56] References Cited

U.S. PATENT DOCUMENTS

| | | | |
|---|---|---|---|
| 3,304,307 | 2/1967 | Mizzoni | 546/194 |
| 3,595,865 | 7/1971 | Sorenson et al. | 260/290 |
| 3,944,566 | 3/1976 | Winter et al. | 260/326 |
| 4,070,373 | 1/1978 | Winter et al. | 260/333 |
| 4,626,542 | 12/1986 | King et al. | 514/325 |
| 4,826,853 | 5/1989 | Piwinski et al. | 514/290 |
| 4,996,321 | 2/1991 | Baldwin et al. | 546/194 |
| 5,089,496 | 2/1992 | Piwinski et al. | 514/253 |
| 5,104,876 | 4/1992 | Piwinski et al. | 514/254 |
| 5,151,423 | 9/1992 | Piwinski et al. | 514/259 |

FOREIGN PATENT DOCUMENTS

| | | |
|---|---|---|
| 0456183 | 11/1991 | European Pat. Off. . |
| 0515158A1 | 11/1992 | European Pat. Off. . |
| WO88/03138 | 5/1988 | WIPO . |
| WO89/10369 | 11/1989 | WIPO . |
| WO89/10363 | 11/1989 | WIPO . |

OTHER PUBLICATIONS

Kaiser, et al., J. Med. Chem 15:665–673 (Jun. 1972).
Villani, et al., J. Med. Chem 15:750–754 (Jul. 1972).

*Primary Examiner*—C. Warren Ivy
*Assistant Examiner*—Raymond Covington
*Attorney, Agent, or Firm*—James M. Gould

[57] ABSTRACT

Disclosed are compounds of Formula I:

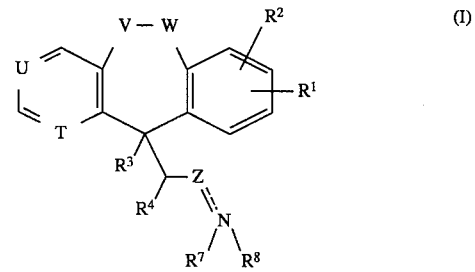

or a pharmaceutically acceptable salt or solvate thereof, wherein:

$R^3$ is alkyl, alkenyl, alkynyl, aryl, alkaryl, aralkyl, cycloalkyl, acyloxymethyl, alkoxy, alkoxymethyl, or alkyl substituted with cycloalkyl;

$R^4$ is H, alkyl, alkenyl, alkoxy, or —OH.

Also disclosed are pharmaceutical compositions containing compounds of Formula I, methods for inhibiting tumor necrosis factor-α and methods for treating septic shock, inflammation, or allergic disease by administering a compound of Formula I.

24 Claims, No Drawings

TRICYCLIC DERIVATIVES, COMPOSITIONS AND METHODS OF USE

FIELD OF THE INVENTION

The present invention relates to tricyclic derivatives, pharmaceutical compositions and methods of using such derivatives. The compounds of the present invention inhibit tumor necrosis factor α ("TNF-α").

BACKGROUND OF THE INVENTION

Tumor necrosis factor α ("TNF-α") is a polypeptide cytokine known to induce a variety of inflammatory and metabolic processes in vivo. See, e.g., *Ann. Rev. Immunol.* 7:625 (1989). However, overproduction or inappropriate production of TNF-α has been shown to be involved in several pathological conditions, including septic shock and various allergic diseases and inflammatory conditions. See, e.g., *Immunol Res.* 10:122 (1991), *Science* 229:869 (1985) and *Proc. Natl. Acad. Sci.* 89:7375 (1992). Thus, compounds that could inhibit TNF-α would be quite valuable in treating these conditions.

In view of the substantial interest in agents that inhibit TNF-α, the identification of compounds having anti-TNF-α activity would be a valuable contribution to the art. This invention provides just such a contribution by providing novel compounds having anti-TNF-α activity. In addition, this invention provides methods of using such compounds.

SUMMARY OF THE INVENTION

We have now unexpectedly found that compounds having the general formula I (set forth below) provide surprisingly good activity as inhibitors of tumor necrosis factor α (TNF-α). More specifically, we believe that the compounds of formula I provide this activity by inhibiting the biosynthesis of TNF-α. In view of this surprising anti-TNF-α activity, it is believed that compounds of formula I are useful in the relief of septic shock, allergic diseases, and inflammatory conditions.

Formula I is as follows:

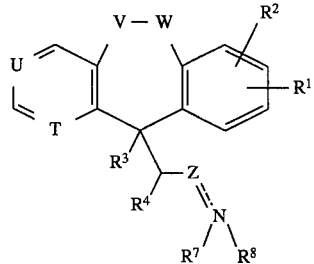

or a pharmaceutically acceptable salt or solvate thereof, wherein:

one of T and U represents N and the other represents =CH; or each of T and U represents =CH—;

one of V and W represents oxygen and the other represents —CH$_2$—; or each of V and W represents —CH$_2$—;

$R^1$ and $R^2$ are each independently selected from the group consisting of H and halogen;

$R^3$ is alkyl, alkenyl, alkynyl, aryl, alkaryl, aralkyl, cycloalkyl, acyloxymethyl, alkoxy, alkoxymethyl, or alkyl substituted with cycloalkyl;

$R^4$ is H, alkyl, alkenyl, alkoxy, or —OH;

Z- - - - -N represents an optional double bond; when Z- - - - -N is a double bond, Z represents —CH=, or —CH$_2$C(R$^5$)=, wherein $R^5$ is H or lower alkyl; and $R^7$ and $R^8$ together represent OR$^9$;

when Z- - - - -N represents a single bond, Z represents a direct bond, —CH$_2$—, —CH=CH—, or —CH$_2$C(R$^5$)(R$^6$)—, wherein $R^5$ and $R^6$ are independently H or lower alkyl (provided that, when $R^3$ is —CH$_3$, Z is not —(CH$_2$)$_2$—); and $R^7$ and $R^8$ are independently H, alkyl, alkenyl, alkynyl, aryl, alkaryl, aralkyl, cycloalkyl, —OR$^9$; —C(O)OR$^{10}$; —CH$_2$C(O)OR$^9$; —C(O)R$^{10}$; —SO$_2$R$^{10}$; —CO-4-pyridyl-N-oxide; —(CH$_2$)$_n$—N(CH$_3$)$_2$, where n is 2 to 4; —(CH$_2$)$_m$O(CH$_2$)$_j$OH, where m and j are independently 2 or 3;

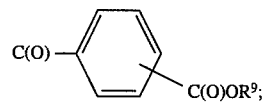

or $R^7$ and $R^8$ together form either a five-membered or a six-membered ring optionally substituted with COOR$^9$; a six-membered ring containing NR$^{10}$; or a five-membered ring fused to a benzene ring;

$R^9$ is H or lower alkyl; and $R^{10}$ is alkyl or aryl.

More preferred compounds of this invention are represented by Formula I wherein $R^3$ is alkoxy, and more preferably wherein $R^3$ is ethoxy.

More preferred compounds also include those of Formula I wherein $R^3$ is alkyl. When $R^3$ is alkyl, $R^3$ is preferably an alkyl group other than —CH$_3$, more preferably an alkyl group having from two to six carbon atoms, and more preferably still, $R^3$ is propyl.

More preferred compounds also include those of Formula I wherein $R^3$ is cyclopropylmethyl, and more preferred compounds also include those of Formula I wherein $R^3$ is allyl.

More preferred compounds also include those of Formula I wherein each of T and U represent =CH—.

Preferably, $R^7$ and $R^8$ are independently H, alkyl, alkenyl, alkynyl, aryl, alkaryl, or aralkyl. When $R^7$ and $R^8$ and N taken together form either a five-membered ring, a six-membered ring, or a five-membered ring fused to a benzene ring, the portion of the 5- or 6-membered ring represented by $R^7$ and $R^8$ is preferably carbocyclic optionally having a nitrogen atom substituted for one of the carbon atoms.

Representative compounds of this invention include, but are not limited to:

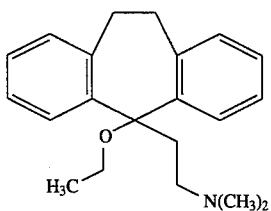

-continued
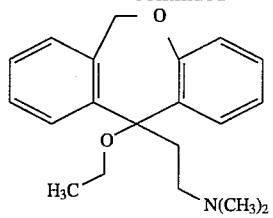 (IB)
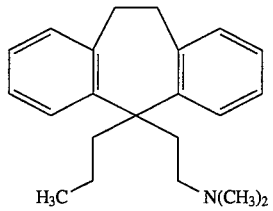 (IC)
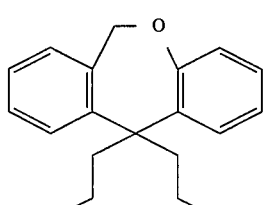 (ID)
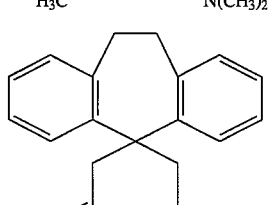 (IE)
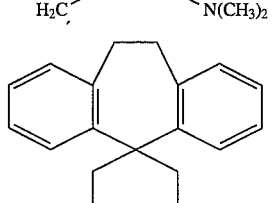 (IF)
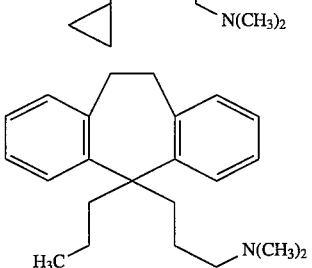 (IG)
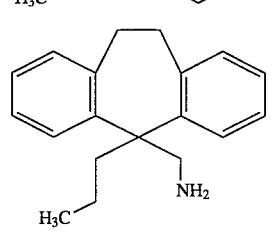 (IH)
-continued
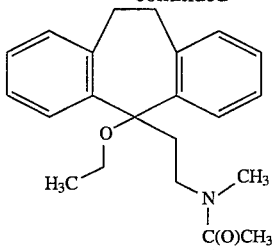 (IJ)
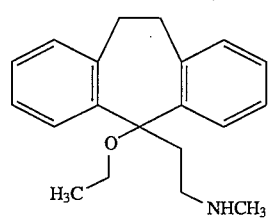 (IK)
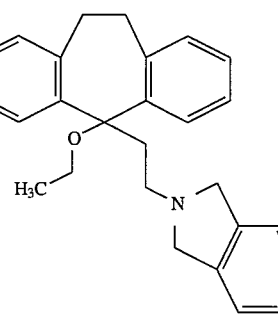 (IL)
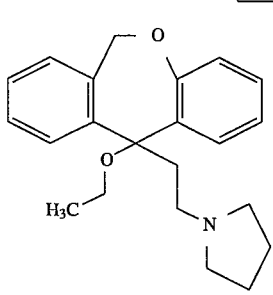 (IM)
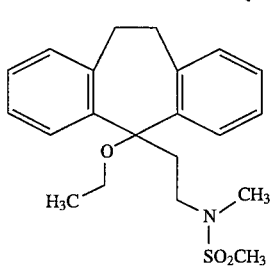 (IN)
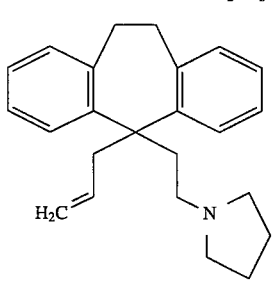 (IO)

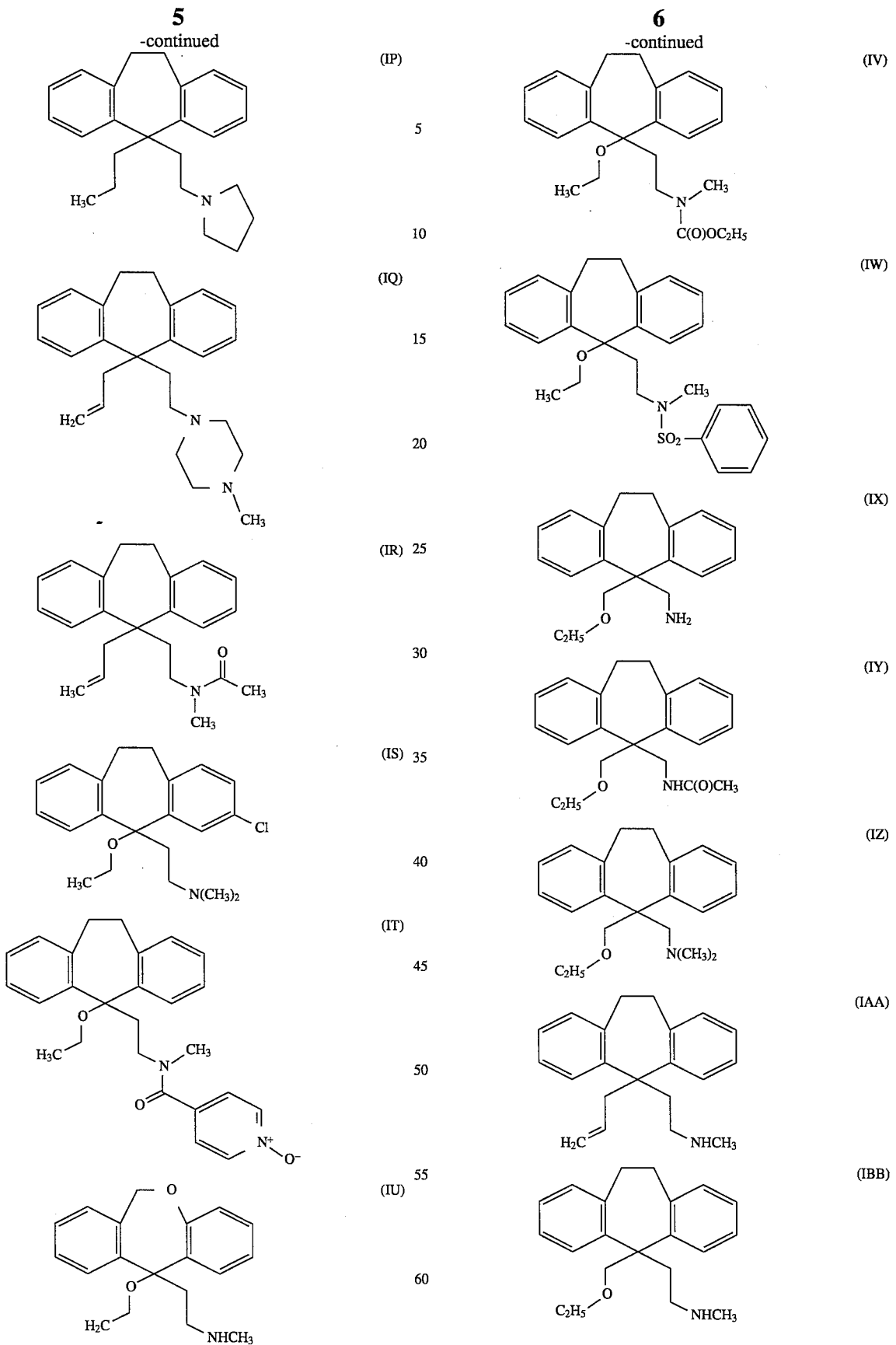

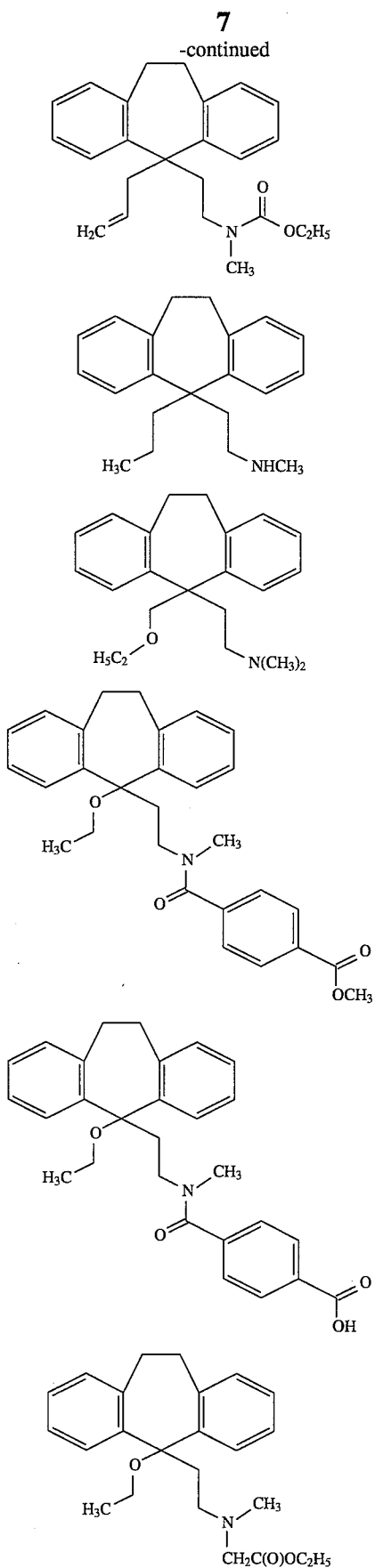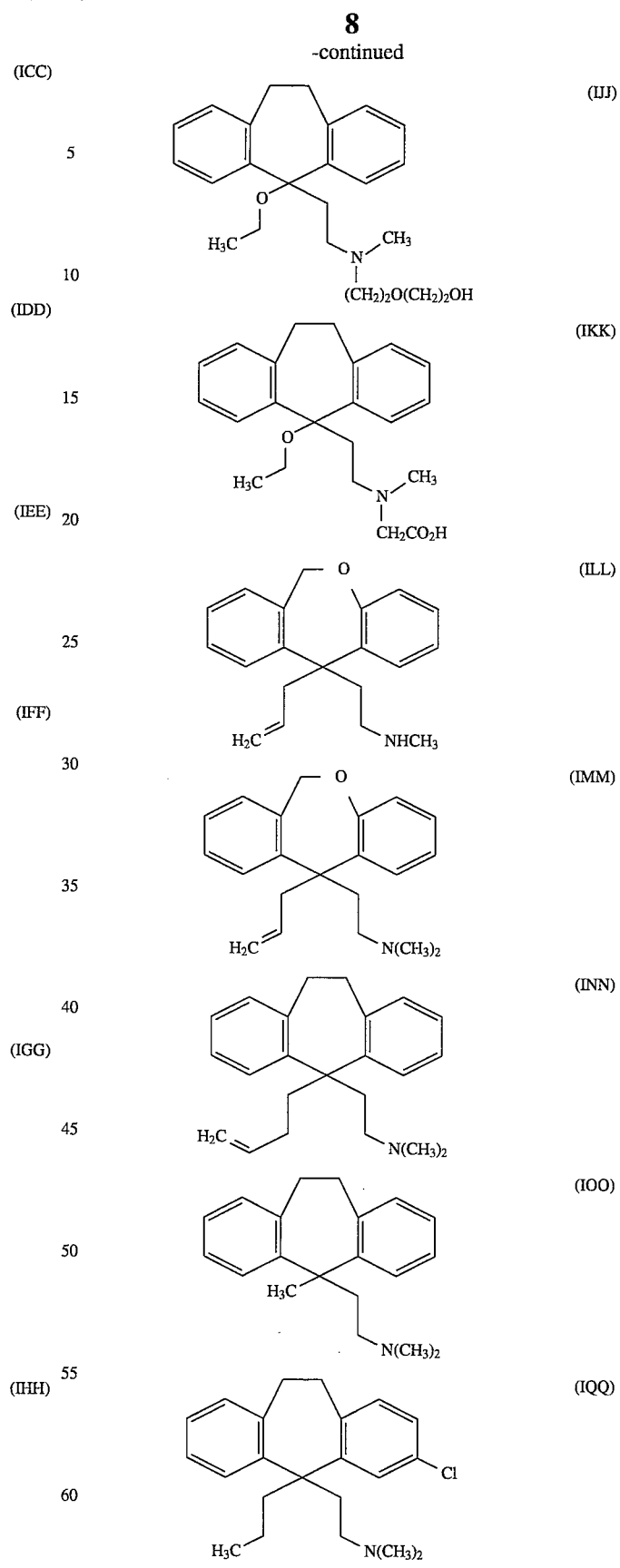

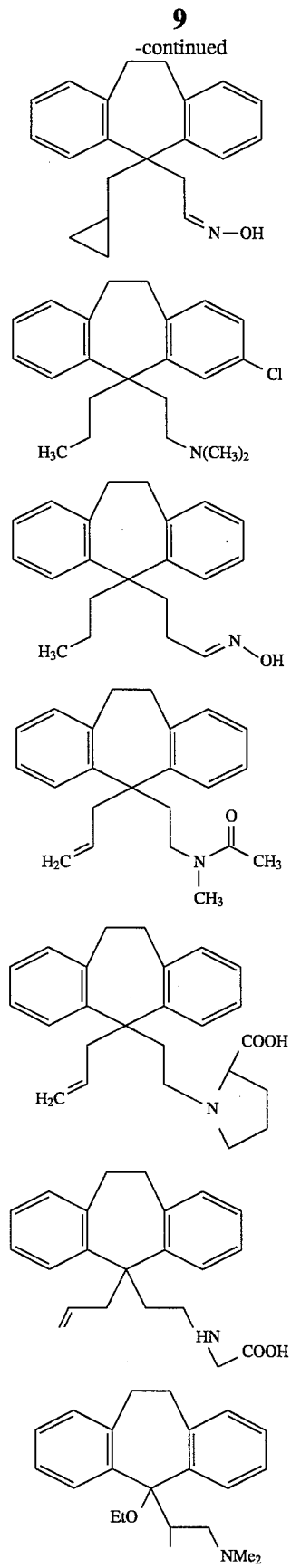

This invention also provides a pharmaceutical composition comprising an effective amount of a compound of Formula I in combination with a pharmaceutically acceptable carrier.

In addition, this invention provides a method for inhibiting TNF-α in a mammal comprising administering to the mammal an amount of a compound of Formula I effective to inhibit TNF-α.

In view of the surprising anti-TNF-α activity of compounds of formula I, this invention provides the following methods of treatment:

a method for treating inflammation in a mammal comprising administering to the mammal an effective anti-inflammatory amount of a compound of Formula I;

a method for treating septic shock in a mammal comprising administering to the mammal an effective anti-septic shock amount of a compound of Formula I; and a method for treating allergic reaction in a mammal comprising administering to the mammal an effective anti-allergic amount of a compound of Formula I.

The present invention will be described in detail below in connection with several preferred embodiments. However, additional embodiments of the present invention will be apparent to those having ordinary skill in the art.

DETAILED DESCRIPTION OF THE INVENTION

As used herein, the following terms are used as defined below unless otherwise indicated:

alkyl—(including the alkyl portions of alkoxy and cycloalkyl)—represents straight and branched carbon chains and contains from one to twenty carbon atoms, preferably one to six carbon atoms;

alkenyl—(including the alkenyl portions of cycloalkenyl) represents straight and branched carbon chains having at least one carbon to carbon double bond and containing from 2 to 12 carbon atoms, preferably from 2 to 6 carbon atoms;

alkynyl—represents straight and branched carbon chains having at least one carbon to carbon triple bond and containing from 2 to 12 carbon atoms, preferably from 2 to 6 carbon atoms;

aryl—represents a carbocyclic group (preferably phenyl or substituted phenyl) containing from 6 to 14 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, cyano, cycloalkyl, alkenyloxy, alkynyloxy, —SH, —S(O)$_e$R$^{12}$ (wherein e is 1 or 2 and R$^{12}$ is alkyl or aryl), —CF$_3$, amino, alkylamino, dialkylamino, —COOR$^{12}$ or —NO$_2$;

acyl—(including the acyl portions of acyloxy) represents —C(O)-alkyl, —C(O)-alkenyl, —C(O)-alkynyl, —C(O)-cycloalkyl, —C(O)-cycloalkenyl or —C(O)-cycloalkynyl;

alkaryl—represents an aryl group, as defined above, in which an alkyl group, as defined above, is substituted for one of the aryl H atoms;

alkoxy—represents an alkyl group, as defined above, attached to a molecule through an oxygen molecule (—O-alkyl);

alkoxymethyl—represents an alkoxy group as defined above attached to a molecule through a methylene group;

aralkyl—represents an alkyl group, as defined above, in which an aryl group, as defined above, is substituted for one of the alkyl H atoms;

and halo—represents fluoro, chloro, bromo and iodo.

Certain compounds of the invention may exist in different isomeric (e.g., enantiomers and diastereoisomers) as well as conformational forms. The invention contemplates all such isomers both in pure form and in admixture, including racemic mixtures. Tautomeric forms are also included.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Lines drawn into the ring systems indicate that the indicated bond may be attached to any of the substitutable ring carbon atoms.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The invention disclosed herein is exemplified by the following preparative examples, which should not be construed to limit the scope of the disclosure. Alternative synthetic pathways and analogous structures within the scope of the invention may be apparent to those of ordinary skill in the art. Further, those skilled in the art will recognize that the reactions are conducted under conditions, e.g., temperature, that will allow the reaction to proceed at a reasonable rate to completion. Unless indicated otherwise, the substituents for the formulas given hereinafter have the same definition as those of Formula I.

PREPARATIVE METHODS AND REACTION SCHEMES

Scheme 1

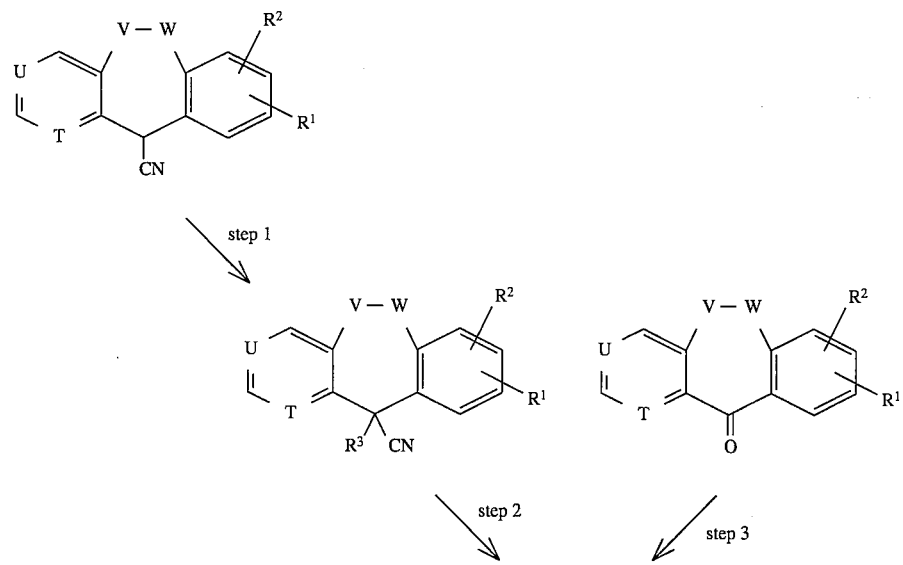

-continued
Scheme 1

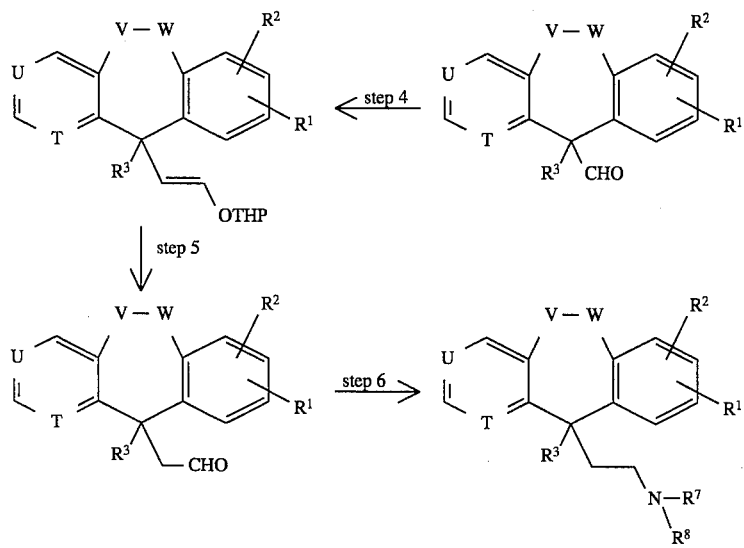

Step 1: This step is preferably carried out by first adding a strong base (e.g. lithium diisopropylamide, potassium bis(trimethylsilyl)amide, sodium hydride, or potassium hydride) in an inert solvent (e.g. ether such as diethyl ether, tetrahydrofuran, or dioxane) with a cosolvent if necessary (e.g. N,N-dimethylformamide, 1,3-dimethyl-3,4,5,6-tetrahydro-2(1H)-pyrimidinone, or hexamethylphosphoramide) under an inert atmosphere (nitrogen or argon). Subsequently, the alkylating agent $R^3L$ is added wherein L represents a good leaving group, e.g. L can be chloride, bromide, iodide, mesylate, or tosylate. Any suitable temperature can be used with preferable temperatures for the deprotonation between −78° C. and 0° C. and for the alkylation between 25° C. and 70° C.

Step 2: This step is preferably carried out with any suitable reducing agent (e.g. diisobutylaluminum hydride, lithium triethoxyaluminum hydride, or sodium aluminum hydride) in an inert solvent such as ether (e.g. diethyl ether, tetrahydrofuran, or dioxane) at temperatures preferably between −78° C. and 25° C. under an inert atmosphere (nitrogen or argon).

Step 3: This step is preferably carried out with the reagent diethyl N-benzylidenaminoalkylphosphonate and two equivalents of n-butyl lithium in an inert solvent such as ether (e.g. diethyl ether, tetrahydrofuran, or dioxane) under an inert atmosphere (nitrogen or argon) to generate a metalloenamine. The metalloenamine is alkylated at temperatures preferably between −78° C. and 25° C. with $R^3L$ wherein L represents a good leaving group, e.g. L can be chloride, bromide, iodide, mesylate, or tosylate. Subsequent acid hydrolysis of the enamine gives the aldehyde product.

Step 4: This step is preferably carried out with the reagent diethyl [(2-tetrahydropyranyloxy)methyl]phosphonate and lithium diisopropylamide in an inert solvent such as ether (e.g. diethyl ether, tetrahydrofuran, or dioxane) under an inert atmosphere (nitrogen or argon). Preferred temperature range is −78° C. to 0° C. for addition of the phosphonate reagent and 25° C. to 70° C. for elimination of the phosphonate reagent.

Step 5: This step is preferably carried out with acid (e.g. hydrochloric acid, acetic acid, or tosic acid) in an inert solvent such as ether (e.g. diethyl ether, tetrahydrofuran, or dioxane) with water. Preferred temperature range is 25° C. to 70° C.

Step 6: This step is preferably carried out with a suitably substituted amine (usually as its acid salt e.g. hydrochloride or maleate) and sodium cyanoborohydride in a solvent mixture of ether (e.g. diethyl ether, tetrahydrofuran, or dioxane) and protic solvent (e.g. methanol or ethanol) with 3A sieves. Preferred temperature range is 25° C. to 70° C.

Scheme 2

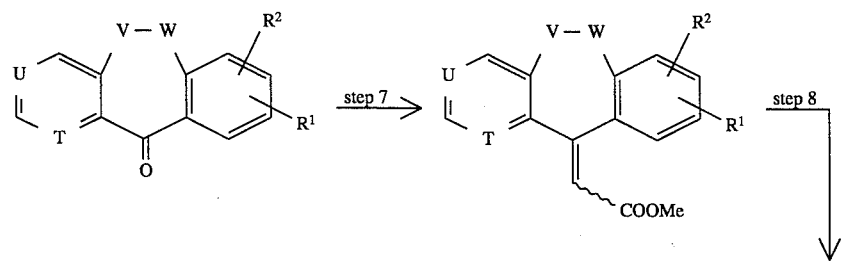

-continued
Scheme 2

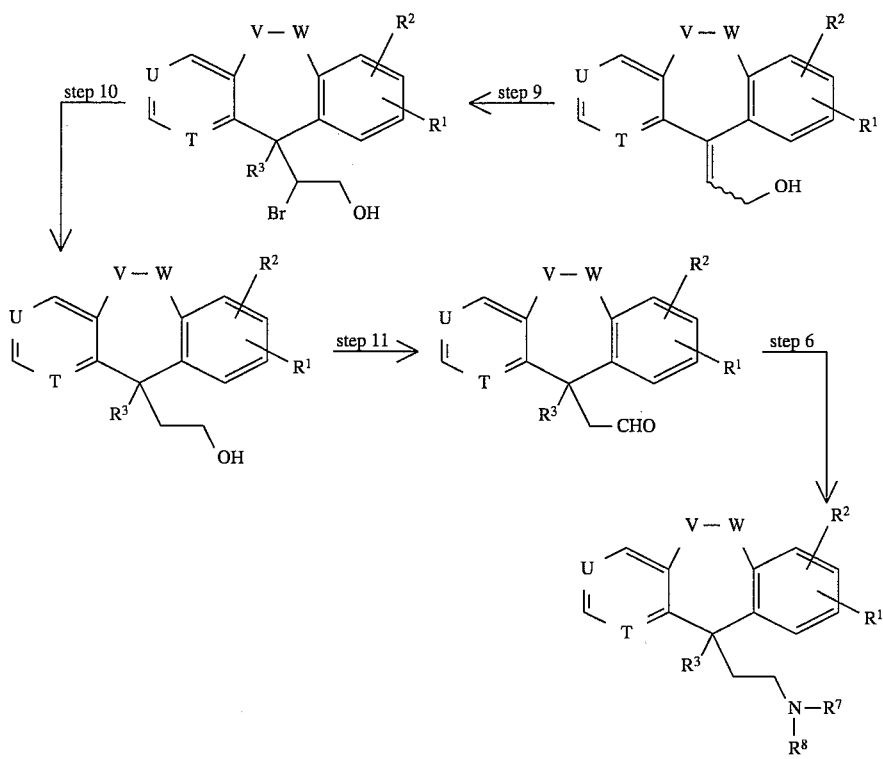

Step 7: This step is preferably carried out with the reagent trimethyl phosphonoacetate and sodium hydride in a polar aprotic solvent (e.g. N,N-dimethylformamide, N,N-dimethylacetamide, or dimethylsulfoxide) under an inert atmosphere (nitrogen or argon). Preferred temperature range is 25° C. to 80° C.

Step 8: This step is preferably carried out with any suitable reducing agent (e.g. diisobutylaluminum hydride, aluminum hydride, or lithium trimethoxyaluminum hydride) in an inert solvent such as ether (e.g. diethyl ether, tetrahydrofuran, or dioxane) at temperatures preferably between −78° C. and 25° C. under an inert atmosphere (nitrogen or argon).

Step 9: This step is preferably carried out with N-bromosuccinimide and $R^3$ as a nucleophile such as methanol, ethanol, or propanol in an inert solvent such as chlorinated hydrocarbons (e.g. dichloromethane, 1,2-dichloroethane, or chloroform) at temperatures between 0° C. and 25° C.

Step 10: This step is preferably carried out with a suitable reducing agent such as tri-n-butyl tin hydride or triphenyl tin hydride and a radical initiator such as azobisisobutyronitrile in an inert solvent (e.g. benzene or toluene). Preferred temperature range is between 80° C. and 110° C.

Step 11: This step is preferably carried out with a suitable oxidizing agent (e.g. pyridinium chlorochromate, chromium trioxide-pyridine, pyridinium dichromate, oxalyl chloride-dimethylsulfoxide, acetic anhydride-dimethylsulfoxide, dicyclohexylcarbodiimidedimethylsulfoxide, or periodinane) in an inert solvent such as chlorinated hydrocarbons (e.g. dichloromethane, 1,2-dichloroethane, or chloroform). Preferred temperature range is between −78° C. and 25° C.

Step 6: This step is described above for Scheme 1.

Scheme 3

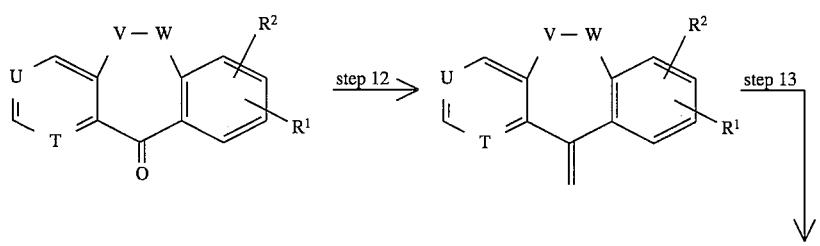

-continued
Scheme 3

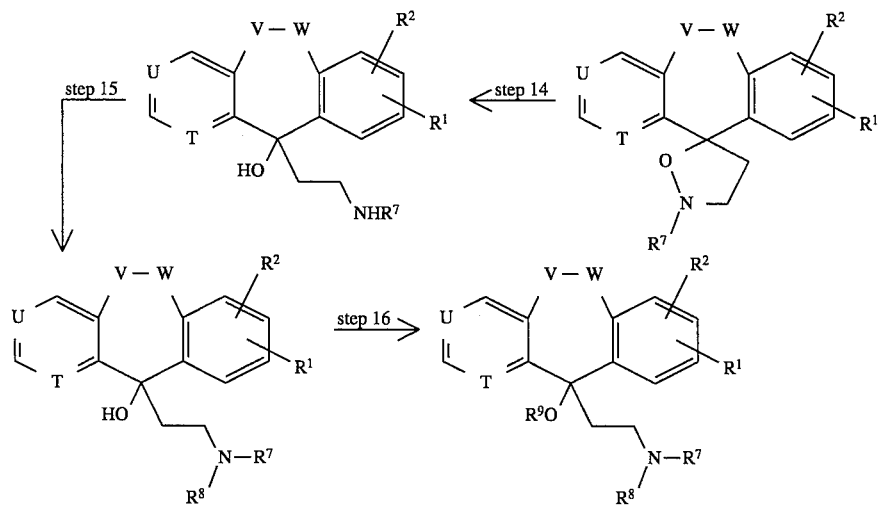

Step 12: This step is preferably carried out with the reagent methyltriphenylphosphonium bromide and base (e.g. sodium hydride or potassium hydride) in dimethylsulfoxide with a temperature range of 50° C. to 80° C. under an inert atmosphere (nitrogen or argon). This step can also be carried out by addition of a Grignard reagent (e.g. methyl magnesium chloride, bromide, or iodide) in an inert solvent such as ether (e.g. diethyl ether, tetrahydrofuran, or dioxane) with preferable temperatures between 0° C. and 25° C. Elimination to give the alkene is catalyzed by a crystal of iodine with sublimation or carried out with acetic anhydride, acetyl chloride, and acetic acid with preferable temperatures between 60° C. and 100° C.

Step 13: This step is preferably carried out with a suitably substituted hydroxylamine, paraformaldehyde, (and a base (e.g. triethylamine or 1,8-diazabicyclo-[5.4.0]undec-7-ene) if the hydroxylamine exists as a salt) in a protic solvent (e.g. ethanol, isopropanol, or butanol) with preferable temperatures between 80° C. and 120° C.

Step 14: This step is preferably carried out with zinc in acetic acid or with zinc and ammonium chloride in an inert solvent (e.g. ether such as tetrahydrofuran or dioxane) with water at a preferred temperature range of 50° C. to 90° C. Alternatively, this step can be carried out with aluminum-nickel alloy and aqueous base (sodium hydroxide or potassium hydroxide) in a protic solvent (e.g. methanol, ethanol, or isopropanol) or by hydrogenation with ammonium formate and palladium on carbon in a protic solvent (e.g. methanol, ethanol, or isopropanol) at a preferred temperature of 25° C.

Step 15: This step is preferably carried out with an alkylating or acylating agent $R^8L$ wherein L represents a good leaving group (e.g. L can be chloride or $R^8L$ can be an anhydride) and a base (e.g. pyridine, triethylamine, collidine, or 1,8-diazabicyclo-[5.4.0]undec-7-ene) in an inert solvent such as chlorinated hydrocarbons (e.g. dichloromethane, 1,2-dichloroethane, or chloroform) under an inert atmosphere (nitrogen or argon). Preferred temperature range is 25° C. to 80° C.

Step 16: This step is preferably carried out by first adding a base (e.g. sodium hydride or potassium hydride) in an inert solvent (e.g. ether such as tetrahydrofuran, dioxane, diglyme) under an inert atmosphere (nitrogen or argon). Subsequently, the alkylating agent $R^9L$ is added wherein L represents a good leaving group, e.g. L can be chloride, bromide, iodide, mesylate, or tosylate. Preferred temperature range is 70° C. to 160° C.

GENERAL PROCESSES

Additional general processes for making compounds of the present invention are as follows:

Preparation of a compound of formula I wherein Z -----N represents a double bond:

A.

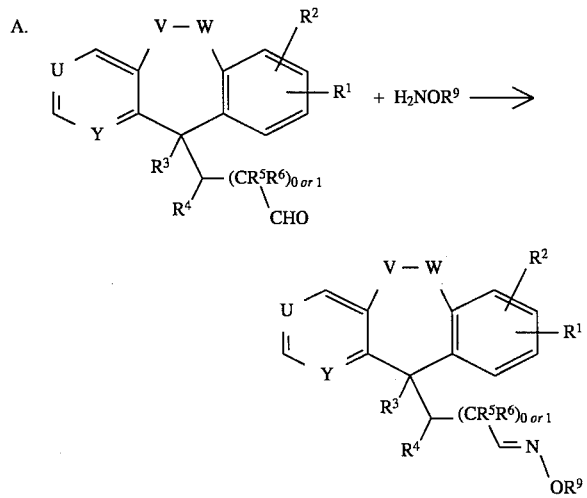

The process is preferably carried out by treating the aldehyde with a hydroxyl amine derivative in an inert solvent such as chlorinated hydrocarbons (e.g. dichloromethane, 1,2-dichloroethane, or chloroform) at ambient temperature. If the hydroxyl amine derivative exists as a salt, the acid can be neutralized by the addition of an amine base such as pyridine, collidine, or triethylamine.

Preparation of a compound of formula I wherein Z ----N represents a single bond:

B. 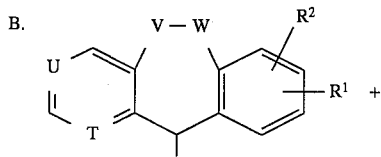

+

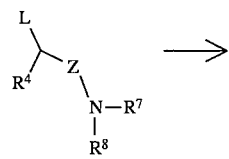

→

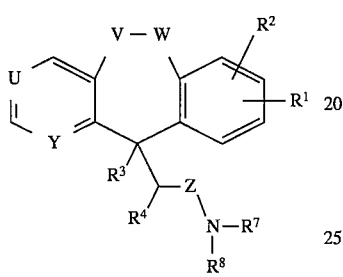

The process is preferably carried out by first adding a strong base (e.g. n-butyl lithium, sec-butyl lithium, sodium amide, potassium amide, lithium diisopropylamide, or potassium bis(trimethylsilyl)amide) to the tricyclic compound in an inert solvent (e.g. ether such as diethyl ether, tetrahydrofuran, or dioxane, or polar solvent such as ammonia, N,N-dimethylformamide, or N,N-dimethylacetamide) under an inert atmosphere (nitrogen or argon). Subsequently, the alkylating agent is added wherein L represents a good leaving group, e.g. L can be chloride, bromide, iodide, mesylate, or tosylate. Any suitable temperature can be used with preferable temperatures between −78° C. and 0° C.

C. 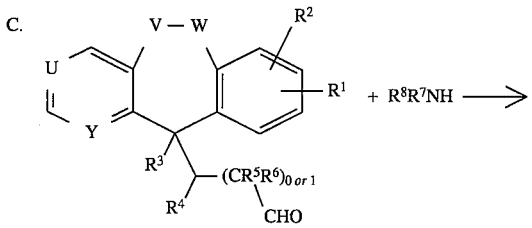

+ R⁸R⁷NH →

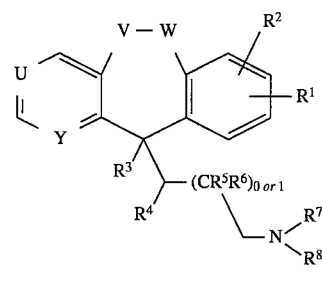

The reductive amination process is preferably carried out by treating the aldehyde with an amine (usually as a salt) in the presence of a reducing agent such as sodium cyanoborohydride and sieves in a suitable solvent mixture of ether (e.g. diethyl ether, tetrahydrofuran, or dioxane) and protic solvent (e.g. methanol or ethanol) at ambient temperature.

D. 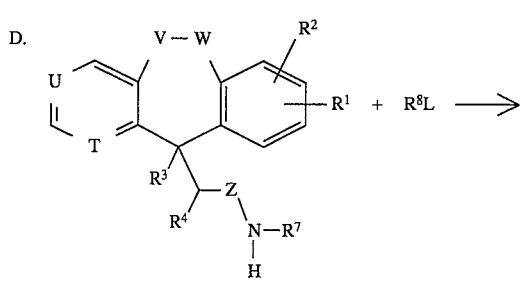

+ R⁸L →

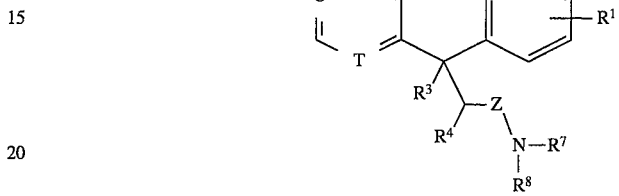

The process is preferably carried out by first adding an amine base (e.g. pyridine, collidine, or triethylamine) in an inert solvent such as chlorinated hydrocarbons (e.g. dichloromethane, 1,2-dichloroethane, or chloroform) or a strong base (n-butyl lithium, sodium hydride, potassium hydride, lithium diisopropyl amide, or potassium bis(trimethylsilyl)amide) in an inert solvent such as ether (e.g. diethyl ether, tetrahydrofuran, or dioxane) or polar aprotic solvent (e.g. N,N-dimethylformamide or N,N-dimethylacetamide) to the tricyclic amine under an inert atmosphere (nitrogen or argon). Subsequently, the alkylating or acylating agent R⁸L is added wherein L represents a good leaving group, e.g. L can be chloride, bromide, iodide, mesylate, or tosylate. Any suitable temperature can be used between −78° C. and 80° C.

E. 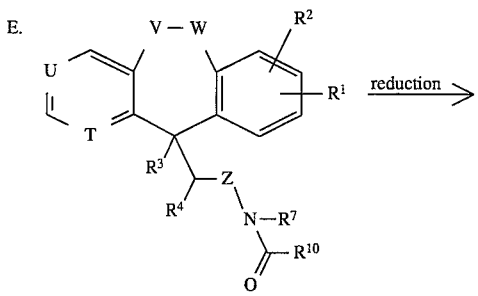 reduction →

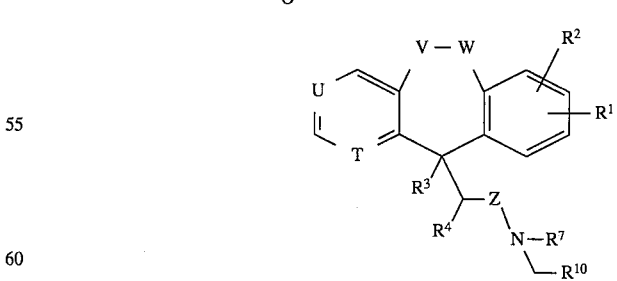

The process is preferably carried out with any suitable reducing agent (e.g. lithium aluminum hydride, alane, borane, or trichlorosilane) in an inert solvent such as ether (e.g. diethyl ether, tetrahydrofuran, or dioxane) at temperatures between 0° C. and 60° C.

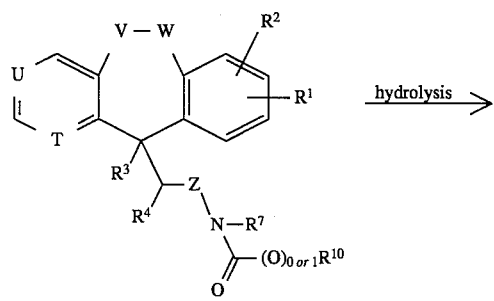

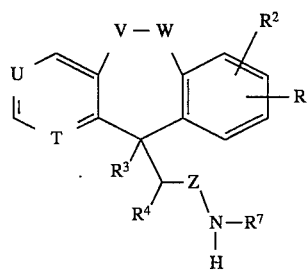

The process is preferably carried out by treating the amide or carbamate compound under basic (e.g. sodium hydroxide, potassium hydroxide, or sodium peroxide in water with ethylene glycol, methanol, ethanol, tetrahydrofuran, dioxane, or diglyme) or acidic (e.g. hydrochloric acid, sulfuric acid, or tosic acid in water with tetrahydrofuran, dioxane, or diglyme) conditions. Any suitable temperature can be used with preferable temperatures between 60° C. and 150° C.

G.

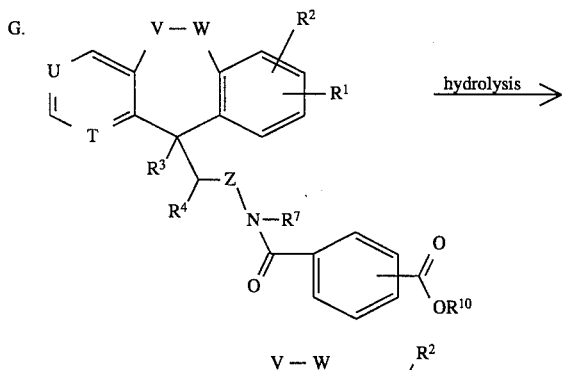

The process is preferably carried out by treating the tricyclic ester compound with a base (e.g. sodium hydroxide or potassium hydroxide) in water with tetrahydrofuran, dioxane, or diglyme. Any suitable temperature can be used with preferable temperatures between 25° C. and 100° C.

Preparation of a compound of formula I wherein Z - - - - -N represents a single bond and $R^3$=alkoxy

H.

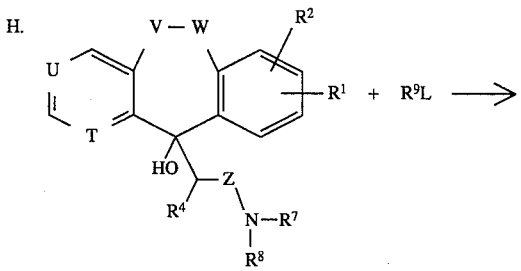

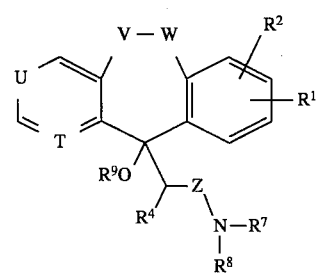

The process is preferably carried out by first adding a strong base (e.g. potassium t-butoxide, sodium hydride, potassium hydride, n-butyl lithium, lithium diisopropylamide, or potassium bis(trimethylsilyl)amide) to the tricyclic alcohol in an inert solvent (e.g. ether such as tetrahydrofuran, dioxane, or diglyme or polar aprotic solvent such as N,N-dimethylformamide or N,N-dimethylacetamide) under an inert atmosphere (nitrogen or argon). Subsequently, the alkylating agent $R^9L$ is added wherein L represents a good leaving group, e.g. L can be chloride, bromide, iodide, mesylate, or tosylate. Any suitable temperature can be used with preferable temperatures between 60° C. and 150° C.

Preparation of a compound of formula I wherein Z - - - - -N represents a single bond and $R^3$=alkyl

I.

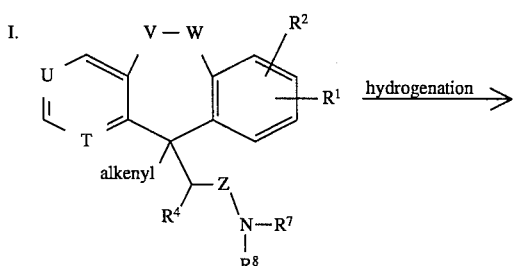

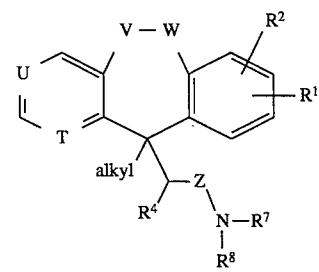

The process is preferably carried out by treating the tricyclic alkene with a catalyst (e.g. palladium on carbon, platinum oxide, or raney nickel) under a hydrogen atmosphere in an inert solvent (e.g. methanol, ethanol, or ethyl acetate) at ambient temperature.

SPECIFIC PREPARATIVE EXAMPLES

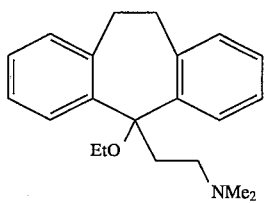

IA

For Compound IA:

Added potassium metal (8.6 g, 0.26 mol) portionwise to 1.0 liter of liquid ammonia with a catalytic amount of iron(III)oxide. Allowed to stir at −33° C. until blue color disappeared to give a gray solution. Added 5-ethoxydibenzosuberone (47.66 g, 0.20 mol) dissolved in 200 mL of ether dropwise via addition funnel. Stirred at −33° C. for 30 mins then added N,N-dimethylaminoethylchloride dissolved in 200 mL of ether dropwise via addition funnel. Warmed gently on steam bath to reflux for 16 hours. Poured onto 1.0 liter of ice, and extracted with ether. Dried combined organic extracts with MgSO$_4$, filtered, and evaporated. Purified crude product by flash chromatography on silica gel eluting with ethyl acetate. Combined appropriate fractions and evaporated to give 29.6 g (48% yield) of 5-ethoxy-5-dimethylaminoethyl-10,11-dihydro-5H-dibenzo[a,d]cycloheptene. Dissolved free base in ethyl acetate, and added one equivalent of maleic acid dissolved in ethanol. Added ether to precipitate the maleate salt.

mp=124°–125° C. mass spectrum: (Cl, CH$_4$) m/e 310 (M+1 for free base)

The following compounds were obtained according to a similar manner:

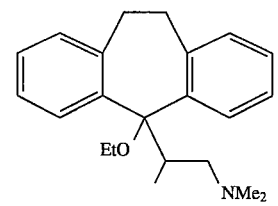

IXX

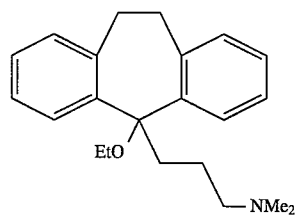

IYY maleate
mp = 154–156° C.
bp = 164–166° C. at 0.7 mmHg

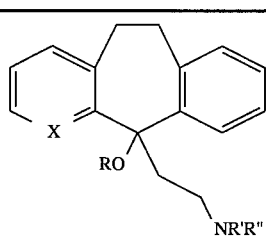

| X | R | NR'R' | salt | mp |
|---|---|---|---|---|
| C | Et | NEt$_2$ | maleate | 120–121° C. |
| C | Et | pyrrolidine | maleate | 142.5–143.5° C. |
| C | Et | piperidine | maleate | 118–119° C. |
| C | Et | (piperidinylmethyl) | HCl | 191–192° C. |
| C | Et | (pyridinyl) |  | 101–103° C. |
| C | iPr | NMe$_2$ | maleate | 154.5–155.5° C. |
| C | Bu | NMe$_2$ | maleate | 114–116° C. |
| C | CH$_2$CHMe$_2$ | NMe$_2$ | fumarate | 132–138° C. |
| N | Me | NMe$_2$ | 0.5 fumarate | 178–180° C. |
| N | Et | NMe$_2$ | fumarate | 165–168° C. |
| N | Et | NEt$_2$ | fumarate | 173–174° C. |
| N | Et | (piperidinylmethyl) | fumarate | 161–163° C. |
| N | Bu | NMe$_2$ | fumarate | 122–124° C. |

| | | | | |
|---|---|---|---|---|
| X | R | NR'R' | salt | mp |

To synthesize an intermediate (step 1 of Scheme 1):

Dissolved diisopropylamine (11.07 g, 0.109 mol) in 150 mL of dry THF and cooled to 0° C. under a nitrogen atmosphere. Added 40.1 mL (0.100 mol) of 2.5M n-butyl lithium in hexane dropwise via addition funnel. Stirred at 0° C. for 10 mins then cooled to −78° C. Added 10,11-dihydro-5H-dibenzo[a,d]cyclohepten-5-nitrile (20.00 g, 0.0912 mol) dissolved in 100 mL of dry THF dropwise via addition funnel. Stirred at −78° C. for 45 mins. Added allyl bromide (14.34 g, 0.119 mol) via syringe, and allowed reaction mixture to warm slowly to room temperature. Stirred at room temperature for 90 mins. Added 250 mL of 0.5N HCl, and separated layers. Extracted aqueous solution with ethyl acetate. Washed combined organic extracts with saturated NaCl, dried with MgSO₄, filtered, and evaporated. Purified crude product by flash chromatography on silica gel eluting with 5% ethyl acetate-hexane then 10% ethyl acetate-hexane. Combined appropriate fractions and evaporated to give 23.65 g (100% yield) of 10,11-dihydro-5-(2-propenyl)-5H-dibenzo[a,d]cyclohepten-5-nitrile.

mp=51°–53° C. mass spectrum: (FAB) m/e 233 (M-CN)

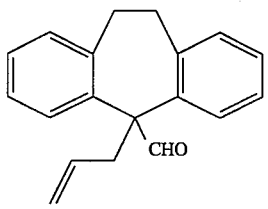

To synthesize an intermediate (step 2 of Scheme 1);

Dissolved 10,11-dihydro-5-(2-propenyl)-5H-dibenzo[a,d]cyclohepten-5-nitrile (24.94 g, 0.0962 mol) in 200 mL of dry dichloromethane, and cooled to −78° C. under a nitrogen atmosphere. Added 1M diisobutylaluminum hydride in dichloromethane (106 mL, 0.106 mol) dropwise via addition funnel. Stirred at −78° C. for 60 mins. then at 0° C. for 2.5 hours. Carefully added 200 mL of 1N HCl then 100 mL of 2N HCl. Stirred at room temperature for 30 mins. Separated layers, and extracted aqueous solution with dichloromethane. Washed combined organic extracts with 1N HCl, saturated NaCl, dried with MgSO₄, filtered, and evaporated. Purified crude product by flash chromatography on silica gel eluting with 10% ethyl acetate-hexane. Combined appropriate fractions and evaporated to give 21.62 (86% yield) of 10,11-dihydro-5-(2-propenyl)-5H-dibenzo[a,d]cyclohepten-5-carboxaldehyde.

mass spectrum: (EI) m/e 221 (M-allyl)

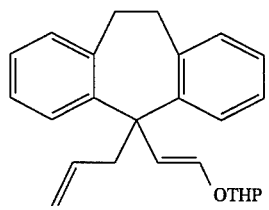

To synthesize an intermediate (step 4 of Scheme 1):

Dissolved diisopropylamine (9.2 g, 0.0910 mol) in 200 mL of dry THF. Cooled to 0° C. under a nitrogen atmosphere. Added 2.5M n-butyl lithium in hexane (35.2 mL, 0.0880 mol) via syringe. Stirred at 0° C. for 10 mins then cooled to −78° C. Added diethyl [(2-tetrahydropyranyloxy)methyl]phosphonate in 45 mL of dry THF via addition funnel. Stirred at −78° C. for 1 hour. Added 10,11-dihydro-5-(2 -propenyl)-5H-dibenzo[a,d]cyclohepten-5-carboxaldehyde in 100 mL of dry THF via addition funnel. Warmed to room temperature then refluxed for 16 hours. Cooled to room temperature, and added 500 mL of saturated NH₄Cl. Separated layers, and extracted aqueous solution with ether. Washed combined organic extracts with saturated NaHCO₃, dried with MgSO₄, filtered, and evaporated. Purified crude product by flash chromatography on silica gel eluting with 3% ether-hexane then 5% ether-hexane. Combined appropriate fractions and evaporated to give 12.7 g (46% yield) of 10,11-dihydro-5-(2-propenyl)-5H-dibenzo[a,d]cyclohepten-5-yl-(2 -tetrahydropyranyloxy-ethene).

mass spectrum: (Cl, CH₄) m/e 361 (M+1)

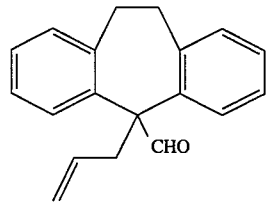

To synthesize an intermediate (step 5 of Scheme 1):

Dissolved 10,11-dihydro-5-(2-propenyl)-5H-dibenzo[a,d]cyclohepten-5-yl-(2-tetrahydropyranyloxy-ethene) (4.82 g, 13.37 mmol) in 50 mL of THF. Added 50 mL of 0.2N HCl, and refluxed for 18 hours. Cooled to room temperature, and added 150 mL of saturated NaHCO$_3$. Extracted with ethyl acetate. Washed combined organic extracts with saturated NaCl, dried (MgSO$_4$), filtered, and evaporated. Purified crude product by flash chromatography on silica gel eluting with 10% ethyl acetate-hexane. Combined appropriate fractions and evaporated to give 3.32 g (90% yield) of 2-[10,11-dihydro-5-(2-propenyl)-5H-dibenzo[a,d]cyclohepten-5-yl]-ethanal).

mass spectrum: (Cl, CH$_4$) m/e 235 (M-allyl)

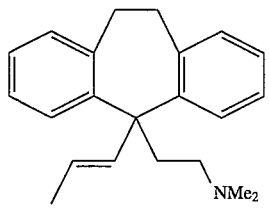

IE

For Compound IE:

Dissolved 2-[10,11-dihydro-5-(2-propenyl)-5H-dibenzo[a,d]cyclohepten-5-yl]-ethanal (1.79 g, 6.48 mmol) in 7 mL of dry THF and 21 mL of dry MeOH. Added 3 A sieves, dimethylamine hydrochloride (2.64 g, 32.38 mmol), and sodium cyanoborohydride (0.407 g, 6.48 mmol). Stirred at room temperature for 72 hours. Added 50 mL of saturated NaHCO$_3$ and 50 mL of dichloromethane. Filtered through celite, and separated layers. Extracted aqueous solution with dichloromethane. Dried combined organic extracts with MgSO$_4$, filtered, and evaporated. Purified crude product by flash chromatography on silica gel eluting with a gradient of 3% MeOH—CH$_2$Cl$_2$, 5% MeOH—CH$_2$Cl$_2$, then 10% MeOH—CH$_2$Cl$_2$. Combined appropriate fractions and evaporated to give 1.41 g (69% yield) of 10,11-dihydro-N,N-dimethyl-5-(2-propenyl)-5H-dibenzo[a,d]cycloheptene-5-(2-ethanamine). Dissolved free base in ethyl acetate and added one equivalent of maleic acid dissolved in ethanol. Evaporated. Added dichloromethane and evaporated. Added ether to precipitate maleate salt.

mp=122°–124° C. mass spectrum: (Cl, CH$_4$) m/e 306 (M+1 for free base)

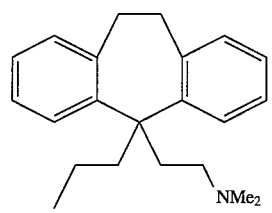

IC

For Compound IC:

Dissolved 10,11-dihydro-N,N-dimethyl-5-(2-propenyl)-5H-dibenzo[a,d]cycloheptene-5-(2-ethanamine) (1.06 g, 3.47 mmol) in 20 mL of absolute ethanol. Added 10 wt % of palladium on carbon catalyst (0.10 g), and shook on Paar shaker at 55 psi of hydrogen pressure for 19 hours. Filtered, and washed catalyst with ethyl acetate. Evaporated filtrate to give 0.973 g (91% yield) of 10,11-dihydro-N,N-dimethyl-5-propyl-5H-dibenzo[a,d]cycloheptene-5-(2-ethanamine). Dissolved free base in ethyl acetate, and added one equivalent of maleic acid dissolved in ethanol. Evaporated. Added minimal dichloromethane then diethyl ether to precipitate maleate salt.

mp=70°–75° C. (soften and foam) mass spectrum: (Cl, CH$_4$) m/e 308 (M+1 for free base)

The following compounds were obtained according to a similar manner:

| X | Y | R | NR'R" | salt | Mass Spectrum |
|---|---|---|---|---|---|
| C | H | allyl | pyrrolidine | maleate | (Cl, CH$_4$) m/e 332 (M+) |
| C | H | allyl | NHMe | HCl | (Cl, CH$_4$) m/e 292 (M + 1) |
| C | H | allyl | NH(CH$_2$)$_3$NMe$_2$ | maleate | (Cl, CH$_4$) m/e 363 (M + 1) |
| C | H | allyl | N—Me-piperazine | maleate | (Cl, CH$_4$) m/e 361 (M + 1) |
| C | H | allyl | t-Bu-glycine | maleate | (Cl, CH$_4$) m/e 392 (M + 1) |
| C | H | allyl | t-Bu-proline | maleate | (Cl, CH$_4$) m/e 432 (M + 1) |
| C | H | propyl | NHMe | maleate | (Cl, CH$_4$) m/e 294 (M + 1) |
| C | H | propyl | pyrrolidine |  | (Cl, CH$_4$) m/e 334 (M+) |
| C | H | EtOCH$_2$ | NHMe | maleate | (FAB) m/e 310 (M + 1) |
| C | H | EtOCH$_2$ | NMe$_2$ | maleate | (Cl, CH$_4$) m/e 324 (M + 1) |
| C | H | methyl | NMe$_2$ | HCl | (Cl, CH$_4$) m/e 280 (M + 1) |
| C | H | cyclopropyl methyl | NMe$_2$ | HCl | (FAB) m/e 320 (M + 1) |
| C | H | hexyl | NMe$_2$ | HCl | (Cl, CH$_4$) m/e 350 (M+) |
| C | H | hexyl | NHMe | maleate | (Cl. CH$_4$) m/e 336 (M + 1) |
| C | H | hexyl | pyrrolidine | maleate | (Cl, CH$_4$) m/e 376 (M + 1) |
| C | H | 1-butenyl | NMe$_2$ | HCl | (Cl, CH$_4$) m/e 320 (M + 1) |
| C | Cl | allyl | NMe$_2$ | maleate | (Cl, CH$_4$) m/e 340 (M + 1) |
| C | Cl | propyl | NMe$_2$ | maleate | (Cl, CH$_4$) m/e 342 (M + 1) |
| O | H | allyl | NHMe | HCl | (Cl, CH$_4$) m/e 294 (M + 1) |
| O | H | allyl | NMe$_2$ | maleate | (Cl, CH$_4$) m/e 308 (M + 1) |
| O | H | propyl | NMe$_2$ | HCl | (Cl, CH$_4$) m/e 310 (M + 1) |

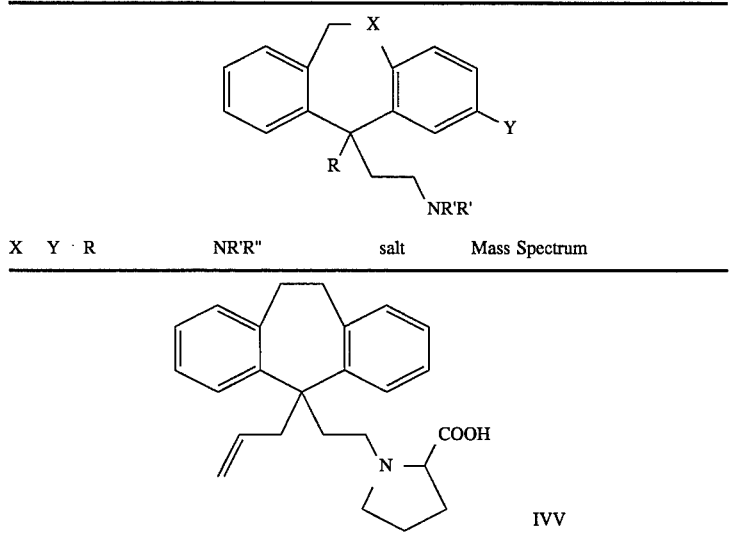

| X | Y | R | NR'R" | salt | Mass Spectrum |
| --- | --- | --- | --- | --- | --- |

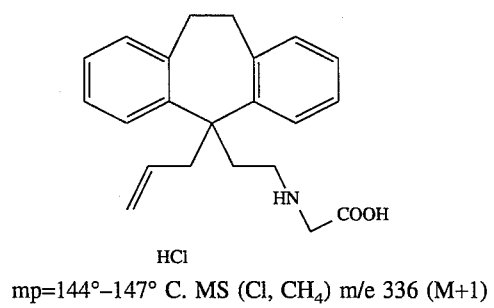

IVV

For Compound IVV:

Dissolved 1,1-dimethylethyl 1-[2-[10,11-dihydro-5-(2-propenyl)-5H-dibenzo[a,d]cyclohepten-5-yl]ethyl]-2-pyrrolidinecarboxylate (2.40 g, 5.56 mmol) in 30 mL of dry THF. Added 25 mL of 4.0M HCl in dioxane, and refluxed for 16 hours on steam bath. Cooled to room temperature, and evaporated. Purified crude product by flash chromatography on silica gel eluting with 5% MeOH—CH$_2$Cl$_2$. Combined appropriate fractions and evaporated to give 0.80 g (40% yield) of 1-[2 -[10,11-dihydro-5-(2-propenyl)-5H-dibenzo [a,d]cyclohepten-5-yl]ethyl]-2 -pyrrolidinecarboxylic acid. Dissolved free base in dichloromethane, and added 3.4M HCl in ether to pH=2. Evaporated, and added ether to precipitate hydrochloride salt.

mp=soften at 125° C. mass spectrum: (CI, CH$_4$) m/e 376 (M+1 for free base)

The following compound was obtained according to a similar manner:

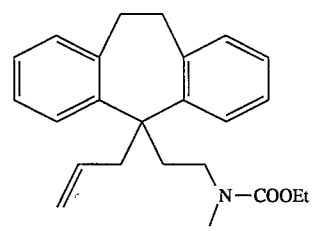

IWW mp=144°–147° C. MS (CI, CH$_4$) m/e 336 (M+1)

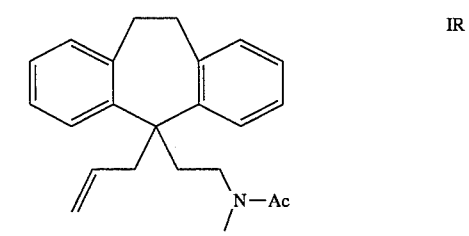

ICC

For Compound ICC:

Dissolved 10,11-dihydro-N-methyl-5-(2-propenyl)-5H-dibenzo[a,d]cycloheptene-5-ethanamine (0.50 g, 1.72 mmol) in 20 mL of dry THF. Added triethylamine (0.29 mL, 0.21 g, 2.06 mmol) and ethyl chloroformate (0.18 mL, 0.20 g, 1.88 mmol). Stirred at room temperature for 5 hours. Added 50 mL of water, and extracted with dichloromethane. Dried combined organic extracts with MgSO$_4$, filtered, and evaporated. Purified crude product by flash chromatography on silica gel eluting with dichloromethane. Combined appropriate fractions, and evaporated to give 0.50 g (81% yield) of ethyl N-[2-[10,11-dihydro-5-(2-propenyl)-5H-dibenzo[a,d]cyclohepten-5-yl]ethyl-N-methylcarbamate.

mass spectrum: (FAB) m/e 364 (M+1)

The following compound was obtained according to a similar manner:

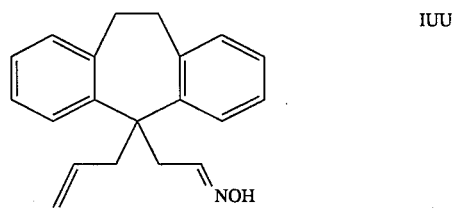

IR mp=139°–141° C. MS (FAB) m/e 334 (M+1)

IUU

For Compound IUU:

Dissolved 2-[10,11-dihydro-5-(2-propenyl)-5H-dibenzo [a,d]cyclohepten-5-yl]-ethanal (1.00 g, 3.62 mmol) in 10 mL of dry dichloromethane under a nitrogen atmosphere. Added 3A sieves, hydroxylamine hydrochloride (0.38 g, 5.43 mmol), and pyridine (0.58 mL, 0.57 g, 7.24 mmol). Stirred at room temperature for 16 hours. Filtered to remove sieve dust, and washed solid with water and dichloromethane. Separated layers of filtrate. Dried organic solution with MgSO$_4$, filtered, and evaporated. Purified crude product by flash chromatography on silica gel eluting with 20% EtOAc-CH$_2$Cl$_2$. Combined appropriate fractions and evaporated to give 0.65 g (62% yield) of 2-[10,11-dihydro-5-(2-propenyl)-

5H-dibenzo[a,d]cyclohepten-5-yl]-ethanone oxime as a colorless oil.

mass spectrum: (Cl, CH$_4$) m/e 291 (M+1)

The following compounds were obtained according to a similar manner:

IRR

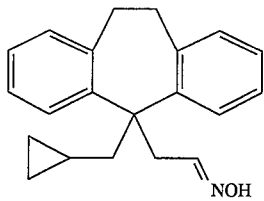

MS(Cl, CH$_4$)m/e 306(M + 1)

ITT

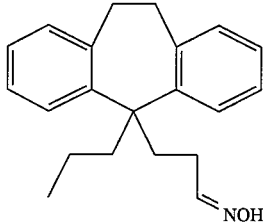

(Cl, CH$_4$)m/e 308(M + 1)

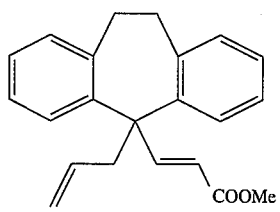

To synthesize an intermediate:

Washed sodium hydride (1.72 g of 60 weight % in oil, 0.0429 mol) two times with hexane under a nitrogen atmosphere. Added 100 mL of dry THF, and cooled to 0° C. Added trimethyl phosphonoacetate (7.81 g, 6.9 mL, 0.0429 mol) dissolved in 15 mL of dry THF dropwise via addition funnel. Hydrogen evolution was observed. Added 50 mL of dry DMF, and stirred at room temperature for 30 mins. Added 10,11-dihydro-5-(2-propenyl)-5H-dibenzo[a,d]cyclohepten-5-carboxaldehyde (7.50 g, 0.0286 mol) dissolved in 25 mL of dry DMF dropwise via addition funnel. Stirred at room temperature for 45 mins then heated at 75° C. for 16 hours. Cooled to room temperature, and added 0.5N NaOH. Extracted with ethyl acetate. Washed combined organic extracts with 0.5N HCl and saturated NaCl, dried with MgSO$_4$, filtered, and evaporated. Purified crude product by flash chromatography on silica gel eluting with 2% ethyl acetate-hexane, 5% ethyl acetate-hexane, then 10% ethyl acetate-hexane. Combined appropriate fractions, and evaporated to give 6.03 g (66% yield) of methyl 3-[10,11-dihydro-5-(2-propenyl)-5H-dibenzo[a,d]cyclohepten-5-yl]-propenoate as a colorless oil.

mass spectrum: (FAB) m/e 319 (M+1)

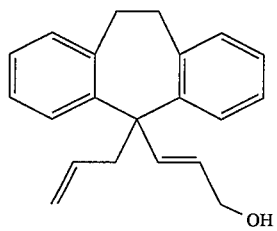

To synthesize an intermediate:

Dissolved methyl 3-[10,11-dihydro-5-(2-propenyl)-5H-dibenzo[a,d]cyclohepten-5-yl]-propenoate (6.00 g, 0.0188 mol) in 80 mL of dry THF. Cooled to 0° C. under a nitrogen atmosphere, and added lithium aluminum hydride (18.8 mL of 1.0M in THF, 0.018 mol) via syringe. Warmed slowly to room temperature and stirred for 20 hours. Recooled to 0° C., and carefully added 0.8 mL water, 0.8 mL of 1N NaOH, and then 2.5 mL of water in sequence. Stirred at room temperature for 1 hour, and filtered through celite. Washed filtrate with saturated NH$_4$Cl, dried with MgSO$_4$, filtered, and evaporated. Purified crude product by flash chromatography on silica gel eluting with 1:4 ethyl acetate:hexane then 1:2 ethyl acetate:hexane. Combined appropriate fractions, and evaporated to give 4.87 g (89% yield) of 3-[10,11-dihydro-5-(2-propenyl)-5H-dibenzo[a,d]cyclohepten-5-yl]-prop-2-en-1-ol as a colorless oil.

mass spectrum: (Cl, CH$_4$) m/e 291 (M+1)

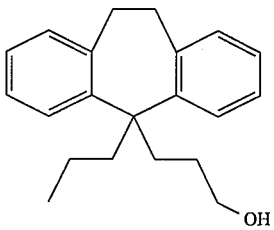

To synthesize an intermediate:

Dissolved 3-[10,11-dihydro-5-(2-propenyl)-5H-dibenzo[a,d]cyclohepten-5-yl]-prop-2-en-1-ol (4.85 g, 16.70 mmol) in 75 mL of absolute ethanol. Added 10% palladium on carbon catalyst (1.20 g), and hydrogenated on Paar shaker at 58 psi of hydrogen pressure for 16 hours. Filtered to remove catalyst, and evaporated filtrate to give 4.43 g (90% yield) of 3-[10,11-dihydro-5-propyl-5H-dibenzo[a,d]cyclohepten-5-yl]-propanol as a colorless oil.

mass spectrum: (Cl, isobutane) m/e 295 (M+1)

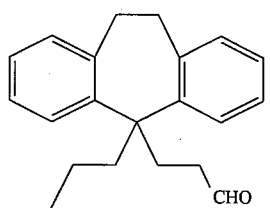

To synthesize an intermediate:

Dissolved oxalyl chloride (1.6 mL, 2.38 g, 0.0187 mol) in 40 mL of dry dichloromethane, and cooled to −78° C. under a nitrogen atmosphere. Added dimethylsulfoxide (2.7 mL, 2.93 g, 0.0374 mol) dissolved in 10 mL of dry dichloromethane dropwise via addition funnel. Stirred for 15 mins at −78° C., and then added 3-[10,11-dihydro-5-propyl-5H-dibenzo[a,d]cyclohepten-5-yl]-propanol (4.41 g, 0.0150 mol) dissolved in 25 mL of dry dichloromethane dropwise via addition funnel. Stirred for 20 mins at −78° C., and then added triethylamine (6.3 mL, 4.55 g, 0.0449 mol). Warmed slowly to room temperature. Added water, and extracted with dichloromethane. Washed combined organic extracts with 0.5N HCl and saturated NaCl, dried with MgSO₄, filtered, and evaporated. Purified crude product by flash chromatography on silica gel eluting with 3% ethyl acetate-hexane, 6% ethyl acetate-hexane, and then 10% ethyl acetate-hexane. Combined appropriate fractions, and evaporated to give 3.85 g (88% yield) of 3-[10,11-dihydro-5-propyl-5H-dibenzo[a,d]cyclohepten-5-yl]-propanal as a colorless oil.

mass spectrum: (Cl, CH₄) m/e 293 (M+1)

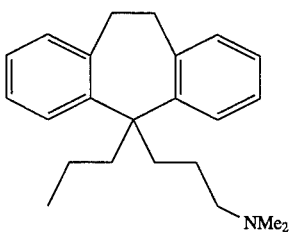

IG

For Compound IG:

Dissolved 3-[10,11-dihydro-5-propyl-5H-dibenzo[a,d]cyclohepten-5yl]-propanal (0.75 g, 2.56 mmol) in 5 mL of dry THF and 10 mL of dry methanol. Added 3A sieves, dimethylamine hydrochloride (1.05 g, 12.82 mmol), and sodium cyanoborohydride (0.161 g, 2.56 mmol). Stirred to room temperature for 24 hours. Added saturated NaHCO₃, and filtered through celite. Extracted filtrate with dichloromethane. Dried combined organic extracts with MgSO₄, filtered, and evaporated. Purified crude product by flash chromatography on silica gel eluting with 3% MeOH—CH₂Cl₂ then 10% MeOH—CH₂Cl₂. Combined appropriate fractions, and evaporated to give 0.53 g (65% yield) of 10,11-dihydro-N,N-dimethyl-5-propyl-5H-dibenzo[a,d]cycloheptenepropanamine as an oil. Dissolved free base in dichloromethane, and added 28.8 weight % HCl-ethanol until acidic. Evaporated to give hydrochloride salt as a foam.

mass spectrum: (Cl, CH₄) m/e 322 (M+1 for free base)

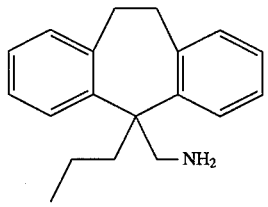

IH

For Compound IH:

Dissolved 10,11-dihydro-5-(2-propenyl)-5H-dibenzo[a,d]cyclohepten-5-nitrile (4.68 g, 0.018 mol) is 150 mL of absolute ethanol, and added sodium borohydride (1.70 g, 0.045 mol). Stirred at room temperature for 15 mins then cooled to 0° C. Added cobalt (II) chloride (4.29 g, 0.018 mol) portionwise. Stirred at room temperature for 30 mins then added additional sodium borohydride (1.70 g, 0.045 mol). Stirred at room temperature for 16 hours. Evaporated, and added 0.5N HCl. Washed with ethyl acetate, and extracted organic solution with 1.0N HCl. Combined acidic aqueous extracts, and made basic with 25 weight % NaOH. Extracted basic solution with dichloromethane. Dried combined organic extracts with MgSO₄, filtered, and evaporated. Purified by flash chromatography on silica gel eluting with ethyl acetate. Combined appropriate fractions, and evaporated to give 1.4 g (30% yield) of 10,11-dihydro-5-propyl-5H-dibenzo[a,d]cycloheptene-5-methanamine as an oil. Dissolved free base in ethyl acetate, and added one equivalent of maleic acid dissolved in ethanol. Added ether to precipitate maleate salt.

mp=174°–175° C. mass spectrum: (Cl, CH₄) m/e 266 (M+1 for free base)

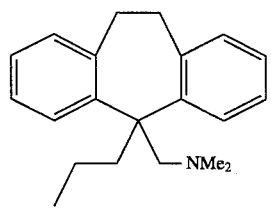

ISS

For Compound ISS:

Dissolved 10,11-dihydro-5-propyl-5H-dibenzo[a,d]cycloheptene-5-methanamine (1.0 g, 3.8 mmol) in 3.5 mL of 96% formic acid. Added 37% aqueous formaldehyde (1.4 mL, 0.57 g, 19.0 mmol). Heated at 100° C. for 23 hours. Cooled to room temperature, and added 25 weight % NaOH. Extracted with dichloromethane. Dried combined organic extracts with MgSO₄, filtered, and evaporated. Purified crude product by flash chromatography on silica gel eluting with 5% MeOH—CH₂Cl₂. Combined appropriate fractions, and evaporated to give 0.90 g (82% yield) of 10,11-dihydro-N,N-dimethyl-5-propyl-5H-dibenzo[a,d]cyclohepten-5-methanamine as an oil. Dissolved free base in ethanol, and added 28 weight % HCl-ethanol until acidic. Added hexane to precipitate hydrochloride salt. Recrystallized salt from ethanol-ether.

mp=220°–221 ° C. mass spectrum: (Cl, CH₄) m/e 294 (M+1 for free base)

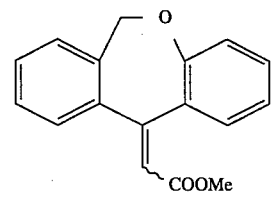

To synthesize an intermediate (step 7 of Scheme 2):

Washed sodium hydride (5.71 g of 60 wt %, 0.143 mol) two times with hexane under a nitrogen atmosphere. Added 170 mL of dry DMF, and cooled to 0° C. Added trimethyl phosphonoacetate (25.99 g, 0.143 mol) dropwise via addition funnel. Hydrogen evolution was observed. Stirred at 0° C. for 15 mins. then at room temperature for 15 mins. Added 6,11-dihydro-dibenz[b,e]oxepin-11-one (15.00 g, 0.0714 mol) dissolved in 70 mL of dry DMF, and heated reaction mixture in a 80° C. oil bath for 45 hours. Cooled to room temperature, and added 250 mL of half saturated NH₄Cl. Extracted with ethyl acetate. Washed combined organic extracts with saturated NaHCO₃, saturated NaCl, dried with MgSO₄, filtered, and evaporated. Purified crude product by flash chromatography on silica gel eluting with a gradient of 5% ethyl acetate-hexane, 7% ethyl acetate-hexane, then 20% ethyl acetate-hexane. Combined appropriate fractions and evaporated to give 3.16 g (21% yield) of starting ketone and 13.16 g (69% yield) of methyl 6,11-dihydrodibenz[b,e]oxepin-11-ylidene acetate.

mass spectrum: (Cl, isobutane) m/e 267 (M+1)

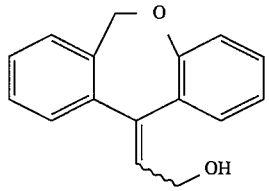

To synthesize an intermediate (step 8 of Scheme 2):

Dissolved methyl 6,11-dihydro-dibenz[b,e]oxepin-11-ylidene acetate (12.68 g, 0.0476 mol) in 100 mL of dry dichloromethane, and cooled to −78° C. under a nitrogen atmosphere. Added 1M diisobutylaluminum hydride in dichloromethane (104.8 ml, 0.105 mol) dropwise via addition funnel over 30 mins. Stirred at −78° C. for 45 mins. then at 0° C., and warmed slowly to room temperature. Recooled to 0° C., and carefully added 200 mL of 1N HCl. Separated layers, and extracted aqueous solution with dichloromethane. Washed combined organic extracts with saturated NaCl, dried with MgSO$_4$, filtered, and evaporated. Purified crude product by flash chromatography on silica gel eluting with 1:2 ethyl acetate:hexane. Combined appropriate fractions, and evaporated to give 11.17 g (98% yield) of 2-[6,11-dihydro-dibenz[b,e]oxepin-11-ylidene]-ethanol as a yellow oil.

mass spectrum: (FAB) m/e 238 (M+)

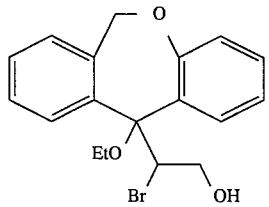

To synthesize an intermediate (step 9 of Scheme 2):

Dissolved 2-[6,11-dihydro-dibenz[b,e]oxepin-11-ylidene]-ethanol (10.90 g, 0.0457 mol) in 175 mL of dichloromethane. Added ethanol (21.07 g, 26.8 mL, 0.457 mol), and cooled to 0° C. under a nitrogen atmosphere. Added N-bromosuccinimide (8.96 g, 0.0503 mol) portionwise. Warmed slowly to room temperature over 60 mins. Added 200 mL of saturated NaHCO$_3$, and separated layers. Extracted aqueous solution with dichloromethane. Dried combined organic extracts with MgSO$_4$, filtered, and evaporated. Purified crude product by flash chromatography on silica gel eluting with 1:4 ethyl acetate:hexane. Combined appropriate fractions, and evaporated to give 14.35 g (86% yield) of 2-bromo-2-[6,11-dihydro-11-ethoxy-dibenz[b,e]oxepin-11-yl]-ethanol as a light yellow oil.

mass spectrum: (Cl, isobutane) m/e 363 (M+)

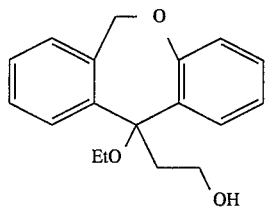

To synthesize an intermediate (step 10 of Scheme 2):

Dissolved 2-bromo-2-[6,11-dihydro-11-ethoxy-dibenz[b,e]oxepin-11-yl]-ethanol (14.34 g, 0.0395 mol) in 150 mL of dry toluene. Added tri-n-butyl tin hydride (17.24 g, 15.9 mL, 0.0592 mol) and AIBN (0.324 g, 0.00197 mol). Refluxed under a nitrogen atmosphere for 18 hours. Cooled to room temperature, and evaporated. Dissolved residue in 300 mL of acetonitrile, and washed with hexane to remove tin by-products. Dried acetonitrile solution with MgSO$_4$, filtered, and evaporated. Purified crude product by flash chromatography on silica gel eluting with 1:4 ethyl acetate:hexane then 1:3 ethyl acetate:hexane. Combined appropriate fractions, and evaporated to give 6.22 g (55% yield) of 2-[6,11-dihydro-11-ethoxydibenz[b,e]oxepin-11-yl]-ethanol as a colorless oil.

mass spectrum: (FAB) m/e 284 (M+)

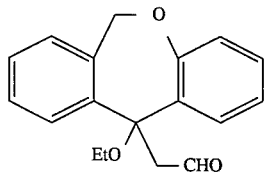

To synthesize an intermediate (step 11 of Scheme 2):

Dissolved oxalyl chloride (3.62 g, 2.5 mL, 0.0285 mol) in 30 mL of dry dichloromethane, and cooled to −78° C. under a nitrogen atmosphere. Added dimethylsulfoxide (4.45 g, 4.0 mL, 0.0570 mol) in 10 mL of dry dichloromethane dropwise via addition funnel. Carbon monoxide and carbon dioxide evolution observed. Stirred at −78° C. for 15 mins. Added 2-[6,11-dihydro-11-ethoxydibenz[b,e]oxepin-11-yl]-ethanol (6.75 g, 0.0237 mol) dissolved in 30 mL of dry dichloromethane dropwise via addition funnel. Stirred at −78° C. for 15 mins. then added triethylamine (7.21 g, 9.9 mL, 0.0712 mol). Warmed slowly to room temperature. Added 150 mL of water, and separated layers. Extracted aqueous solution with dichloromethane. Washed combined organic extracts with 0.5N HCl and then saturated NaCl, dried with MgSO$_4$, filtered, and evaporated. Purified crude product by flash chromatography on silica gel eluting with 5% ethyl acetatehexane then 10% ethyl acetate-hexane. Combined appropriate fractions, and evaporated to give 3.47 g (52% yield) of 2-[6,11-dihydro-11-ethoxydibenz[b,e]oxepin-11-yl]-ethanal as a colorless oil.

mass spectrum: (FAB) m/e 282 (M+)

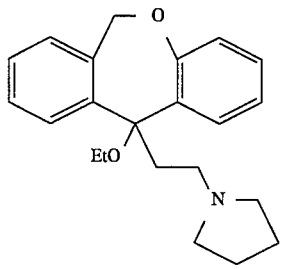 IM

For Compound IM:

Dissolved 2-[6,11-dihydro-11-ethoxy-dibenz[b,e]oxepin-11-yl]-ethanal (500 mg, 1.77 mmol) in 2 mL of dry THF and 6 mL of dry methanol. Added 3 A sieves, pyrrolidine hydrochloride (952 mg, 8.85 mmol), and then sodium cyanoborohydride (111 mg, 1.77 mmol). Stirred at room temperature under a drying tube for 24 hours. Added 30 mL of saturated $K_2CO_3$ and 15 mL of dichloromethane. Filtered through celite, and separated layers. Extracted aqueous solution with dichloromethane. Dried combined organic extracts with $MgSO_4$, filtered, and evaporated. Purified crude product by flash chromatography on silica gel eluting with 3% MeOH—$CH_2Cl_2$ then 10% MeOH—$CH_2Cl_2$. Combined appropriate fractions, and evaporated to give 0.21 g (35% yield) of 1-[2-(11-ethoxy-6,11-dihydrodibenz[b,e]oxepin-11-yl)ethyl]pyrrolidine as a colorless oil. Dissolved free base in ethyl acetate, and added one equivalent of maleic acid dissolved in ethanol. Evaporated, added ethyl acetate, and evaporated again. Added ether to precipitate maleate salt.

mp=108°–110° C. (foams) mass spectrum: (FAB) m/e 338 (M+1 for free base)

The following compounds were obtained according to a similar manner:

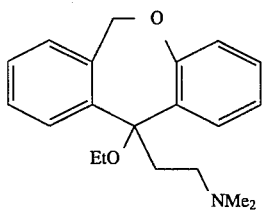 IB maleate
MS(FAB)m/e 312(M + 1)

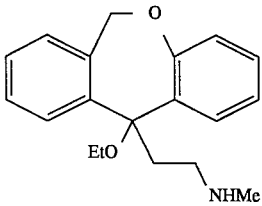 IU maleate
(SIMS)m/e 298(M + 1)

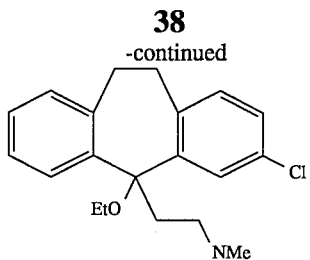 IS maleate
(Cl, CH₄)m/e 296(M + 1)

To synthesize an intermediate (step 13 of Scheme 3):

Dissolved 1-methylene-2,3,6,7-dibenzo-2,6-cycloheptadiene (2.0 g, 9.7 mmol), N-benzylhydroxylamine hydrochloride (1.91 g, 12.0 mmol), triethylamine (1.21 g, 1.7 mL, 12.0 mmol), and paraformaldehyde (0.36 g, 12.0 mmol) in 40 mL of absolute ethanol. Refluxed reaction mixture for 75 hours, and cooled to room temperature. Evaporated, and added water. Extracted aqueous solution with dichloromethane. Dried combined organic extracts with $MgSO_4$, filtered, and evaporated. Purified crude product by flash chromatography on silica gel eluting with 10% $CH_2Cl_2$-hexane. Combined appropriate fractions, and evaporated to give 2.7 g (82% yield) of 10,11-dihydro-2'-phenylmethylspiro[5H-dibenzo[a,d]cycloheptene-5,5'-isoxazolidine as a white solid.

mp=108°–111° C. mass spectrum: (FAB) m/e 342 (M+1)

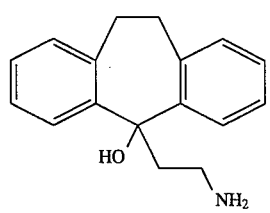

To synthesize an intermediate (step 14 of Scheme 3):

Suspended 10,11-dihydro-2'-phenylmethylspiro[5H-dibenzo[a,d]cycloheptene-5,5'-isoxazolidine (4.1 g, 11.7 mmol) in 400 mL of methanol. Added 10% palladium on carbon (2.0 g) and ammonium formate (3.8 g, 60.3 mmol) dissolved in 100 mL of methanol. Heated reaction mixture at 70° C. for 3 hours. Filtered reaction mixture while hot, and washed catalyst with methanol. Evaporated filtrate, and added saturated $NaHCO_3$. Extracted aqueous solution with dichloromethane. Dried combined organic extracts with $MgSO_4$, filtered, and evaporated. Purified crude product by flash chromatography on silica gel eluting with acetonitrile. Combined appropriate fractions, and evaporated to give 2.20 g (72% yield) of 10,11-dihydro-5-(2-aminoethyl)-5H-dibenzo[a,d]cyclohepten-5-ol as a white solid.

mp=104°–107° C. mass spectrum: (electrospray) m/e 254 (M+1)

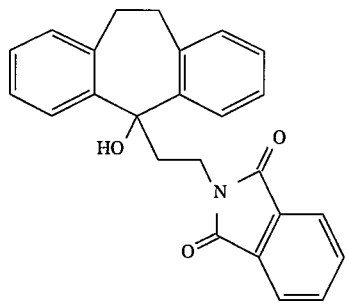

To synthesize an intermediate (step 15 of Scheme 3):

Dissolved 10,11-dihydro-5-(2-aminoethyl)-5H-dibenzo[a,d]cyclohepten-5-ol (3.58 g, 14.1 mmol) and phthalic anhydride (2.1 g, 14.1 mmol) in 30 mL of pyridine, and refluxed for 15 hours. Removed pyridine by evaporation, and added saturated NaHCO$_3$. Extracted aqueous solution with dichloromethane. Washed the combined organic extracts with 1N HCl and then water, dried with MgSO$_4$, filtered, and evaporated. Crystallized product from ether to give 4.50 g (83% yield) of 6-[2-(10,11-dihydro-5-hydroxy-5H-dibenz[a,d]cyclohepten-5-yl)ethyl]-5H-[pyrrolo[3,4-b]pyridine-5,7(6H)-dione as a white solid.

mp=152°–154° C. mass spectrum: (FAB) m/e 384 (M+1)

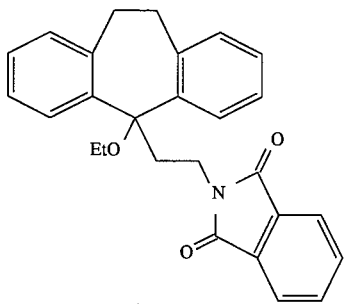

To synthesize an intermediate (16 of Scheme 3):

Washed sodium hydride (0.36 g, 9 mmol, 60 weight % in oil) two times with hexane under a nitrogen atmosphere. Added 5 mL of dry dioxane and then 6-[2-(10,11-dihydro-5-hydroxy-5H-dibenz[a,d]cyclohepten-5-yl)ethyl]-5H-[pyrrolo[3,4-b]pyridine-5,7(6H)-dione (1.15 g, 3 mmol) dissolved in 30 mL of dry dioxane dropwise. Refluxed the reaction mixture for 1 hour. Added ethyl iodide (1.4 g, 0.72 mL, 9 mmol) via syringe, and refluxed for 15 hours. Cooled to room temperature, and evaporated. Added water, and extracted with dichloromethane. Washed combined organic extracts with saturated NaCl, dried with MgSO$_4$, filtered, and evaporated. Purified crude product by chromatography on silica gel eluting with dichloromethane. Combined appropriate fractions, and evaporated to give 0.37 g (30% yield) of 6-[2-(10,11-dihydro-5-ethoxy-5H-dibenz[a,d]cyclohepten-5-yl)ethyl]-5H-[pyrrolo[3,4-b]pyridine-5,7(6H)-dione.

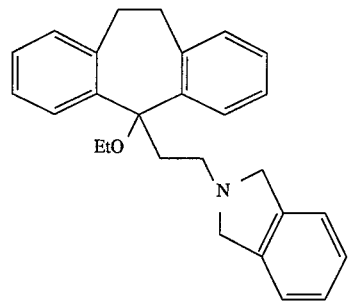

IL

For Compound IL:

Dissolved lithium aluminum hydride (0.15 g, 3.95 mmol) in 5 mL of dry tetrahydrofuran under a nitrogen atmosphere. Added 6-[2-(10,11-dihydro-5-ethoxy-5H-dibenz[a,d]cyclohepten-5-yl)ethyl]-5H-[pyrrolo[3,4-b]pyridine-5,7(6H)-dione (0.35 g, 0.85 mmol) dissolved in 20 mL of dry tetrahydrofuran dropwise via addition funnel. Refluxed reaction mixture for 8 hours, and then cooled to 0° C. Carefully added 0.2 mL of water, 0.2 mL of 15 weight % NaOH, and then 0.6 mL of water to precipitate the aluminum salts. Filtered precipitate, and washed with tetrahydrofuran. Evaporated filtrate. purified crude product by flash chromatography on silica gel eluting with CH$_2$Cl$_2$ then 3% MeOH—CH$_2$Cl$_2$. Combined appropriate fractions and evaporated to give 0. 19 g (59% yield) of 2-[2 -[5-ethoxy-10,11-dihydro-5H-dibenzo[a,d]cyclohepten-5-yl]ethyl]-1,3-dihydro-2H-isoindole as a pink solid.

mp=101°–104° C. mass spectrum: (CI, CH$_4$) m/e 384 (M+1)

The following compound was obtained according to a similar manner:

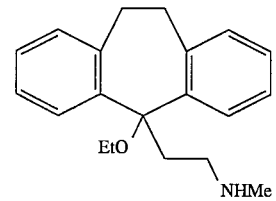

IK

MS (FAB) m/e 296 (M+1 for free base)

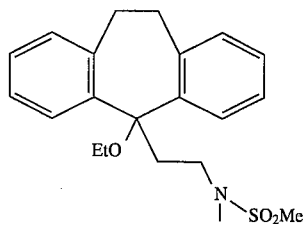

IN

For Compound IN: Dissolved N-[2-(5-ethoxy-10,11-dihydro-5H-dibenzo[a,d]cyclohepten-5-yl)ethyl]-N-methylamine (150 mg, 0.508 mmol) in 5 mL of dry dichloromethane. Cooled to 0° C. under a nitrogen atmosphere, and added triethylamine (0.14 mL, 0.10 g, 1.0 mmol) and then methanesulfonyl chloride (0.06 mL, 0.089 g, 0.76 mmol) dropwise via syringe. Stirred at 0° C. for 90 mins. Added water, and extracted with dichloromethane. Washed the combined organic extracts with sodium phosphate monobasic, 1N NaOH, and then saturated NaCl. Dried with MgSO$_4$, filtered, and evaporated. Purified crude product by flash chromatography eluting with 9:1 hexane:ethyl acetate. Combined appropriate fractions, and evaporated to solid.

Recrystallized from ethyl acetate-hexane to give 92 mg (48% yield) of N-[2-(5-ethoxy-10,11-dihydro-5H-dibenzo[a,d]cycloheptenyl)ethyl]-N-methylmethanesulfonamide as a white solid.

mp=72.5°–73.5° C. mass spectrum: (FAB) m/e 396 (M+1+Na)

The following compounds were obtained according to a similar manner:

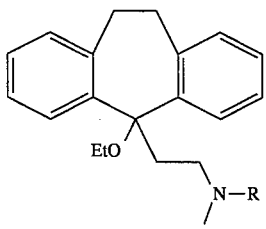

| R | mp | Mass Spectrum |
| --- | --- | --- |
| SO$_2$Ph | oil | (FAB) m/e 436 (M + 1) |
| COMe | 106–109° C. | (FAB) m/e 338 (M + 1) |
| COOEt | oil | (FAB) m/e 368 (M + 1) |
| CH$_2$COOEt | oil | (CI, CH$_4$) m/e 382 (M + 1) |
| CH$_2$CH$_2$OCH$_2$CH$_2$OH | oil | (CI, NH$_3$) m/e 384 (M + 1) |
| COPh(4-COOMe) | oil | (FAB) m/e 458 (M + 1) |
| CO(4-pyridine-N-oxide) | oil | (FAB) m/e 417 (M + 1) |

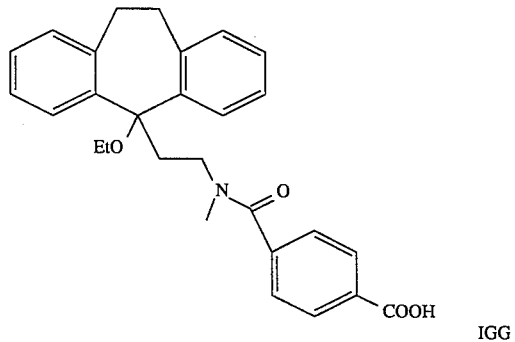

IGG

For Compound IGG:

Dissolved N-[2-[5-ethoxy-10,11-dihydro-5H-dibenzo[a,d]cyclohepten-5-yl]ethyl]-N-methyl-4-methoxycarbonylbenzamide (145 mg, 0.32 mmol) in 12 mL of methanol. Added 12 mL of 2N KOH, and stirred at room temperature for 60 mins. Added sodium phosphate monobasic, and extracted with ethyl acetate. Washed combined organic extracts with saturated NaCl, dried with MgSO$_4$, filtered, and evaporated to give 113 mg (80% yield) of 4-[[N-[2-[5-ethoxy-10,11-dihydro-5H-dibenzo-[a,d]cyclohepten-5-yl]ethyl]-N-methyl]oxo]benzoic acid as a white solid.

mp=148°–150° C. mass spectrum: (FAB) m/e 444 (M+1)

The following compound was obtained according to a similar manner:

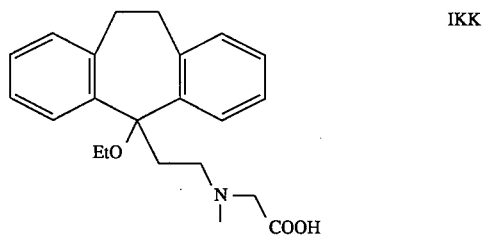

IKK

MS (FAB) m/e 354 (M+1)

As mentioned above, the compounds of formula I exhibit good anti-TNF-α activity. The compounds of the invention are, therefore, useful when TNF-α activity is a factor in a given disease or disorder such as in the case of septic shock and various allergic diseases and inflammatory conditions.

The anti-TNF-α properties of the compounds of the present invention may be demonstrated by use of a standard in vitro pharmacological testing procedure as described below. This test procedure is a standard test used to determine anti-TNF-α activity and to evaluate the usefulness of said compounds for counteracting the biological effects of TNF-α.

1. In Vitro Study: Inhibition of LPS-Induced TNF-α Production From the Murine Cell Line WEHI-265

1) Cells (obtained from cell cultures containing ≦10$^6$ cells/ml) are suspended at 0.2×10$^6$ cells/ml in complete medium (RpMI1640, with 10% FCS, 10$^{-5}$M 2-ME, 2 mM glutamine and 10 mM HEPES buffer) and plated in CoStar 24 well plates (1.0 ml/well).
2) Compounds are dissolved in the appropriate vehicle at 400 times the concentration to be tested, and 5 μl of compound is added to the wells.
3) LPS (from E. coli 0111:B4) is diluted to 6 μg/ml and 1.0 ml is added to wells.
4) Plates are incubated 20–24 hours in 37° CO$_2$ incubator.
5) Supernatant fluids are collected and analyzed for TNF content as described in J. Immunol., 142:3884.

The results of this procedure are shown in TABLE 1 below.

TABLE 1

| COMPOUND | % INHIBITION AT 10 μM |
| --- | --- |
| IA | 51 |
| IB | 33 |
| IC | 60 |
| ID | 62 |
| IE | 67 |
| IF | 68 |
| IG | 60 |
| IH | 77 |
| IJ | 48 |
| IK | 60 |
| IL | 53 |
| IM | 54 |
| IN | 19 |
| IO | 66 |
| IP | 44 |
| IQ | 68 |
| IR | 61 |
| IT | 14 |
| IU | 25 |

TABLE 1-continued

| COMPOUND | % INHIBITION AT 10 μM |
|---|---|
| IV | 34 |
| IW | 47 |
| IX | 29 |
| IY | 17 |
| IZ | 37 |
| IAA | 56 |
| IBB | 45 |
| ICC | 42 |
| IDD | 59 |
| IEE | 23 |
| IFF | 44 |
| IGG | 4 |
| IHH | 40 |
| IJJ | 53 |
| IKK | 13 |
| ILL | 50 |
| IMM | 70 |
| INN | 75 |
| IOO | 16 |
| IPP | 52 |
| IQQ | 42 |
| IRR | 48 |
| ISS | 67 |
| ITT | 4 |
| IUU | 29 |
| IVV | 14 |

In addition to the in vitro test described above, the following in vivo test was also performed on several of the compounds of the present invention. Although the individual reported values may be subject to a wide margin of error, collectively the in vivo data demonstrates that the compounds of the invention are inhibitors of TNF-α in a mammalian species.

In Vivo Study: Inhibition of LPS-Induced Serum TNF

1) Mice (C57BI/6J males, 6–8 weeks of age) are dosed with the indicated compound (dissolved in CMC suspension vehicle; compounds are given orally or i.p. one hour before LPS challenge).
2) Mice are challenged with LPS (from E. coli 0111:B4; 50 μg i.p.).
3) Mice are bled 90 min after LPS challenge.
4) Sera are analyzed for TNF content by ELISA as described in J. Immunol. 142:3884.

Results are shown in TABLE 2 below.

| Compound | % of inhibition at 25 mg/kg |
|---|---|
| IA | 69 |
| IB | 70 |
| IC | 65 |
| ID | 67 |
| IE | 48 |
| IF | 34 |
| IK | 40 |
| IM | 58 |
| IO | 47 |
| IP | 52 |
| IR | 36 |
| IU | 21 |
| IX | 3 |
| IZ | 0 |
| IAA | 38 |
| IBB | 34 |
| IDD | 31 |
| IEE | 38 |
| IFF | 0 |
| IGG | 0 |

| Compound | % of inhibition at 25 mg/kg |
|---|---|
| ILL | 44 |
| IMM | 32 |
| IRR | 38 |

The effect of the compounds of the present invention against septic shock may be demonstrated by use of a standard pharmacological testing procedure as described below. This test procedure is a standard test used to determine activity against septic shock.

3. In Vivo Study: Inhibition of LPS/Galactosamine-Induced Lethality

1) Mice (C57BI/6J males, 6–8 weeks of age) are dosed with the indicated compound (dissolved in CMC suspension vehicle; compounds are given orally or i.p. one hour before challenge with LPS and d-galactosamine).
2) Mice are challenged i.p. with a mixture of LPS (from E. coli 0111:B4; 100 ng) and d-galactosamine (8 mg).
3) Survival is determined 24 hours after challenge. See procedure published in J. Exp. Med. 165:657 (1987)

Results are shown in TABLE 3 below.

| Compound | # dead/total at 25 mg/kg |
|---|---|
| IA | 0/8 |
| IB | 0/9 |
| IC | 1/9 |
| IE | 0/9 |
| IJ | 8/8 |
| IK | 0/9 |
| IM | 1/8 |
| IN | 6/9 |
| IO | 5/9 |
| IP | 9/9 |
| IS | 3/10 |
| IT | 9/9 |
| IU | 8/9 |
| IW | 8/10 |
| IX | 9/10 |
| IZ | 8/10 |
| IAA | 5/10 |
| IBB | 10/10 |
| IDD | 9/10 |
| IEE | 8/10 |
| IFF | 9/9 |
| IGG | 10/10 |
| ILL | 3/10 |
| IMM | 0/10 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to achieve relief of the symptoms.

DOSAGE FORMS

The following are examples of pharmaceutical dosage forms which contain a compound of the invention. As used therein, the term "active compound" is used to designate the compound

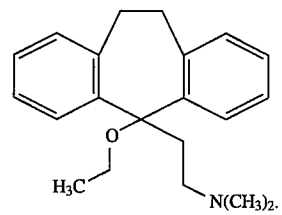

(IA)

The scope of the invention in its pharmaceutical composition aspect is not to be limited by the examples provided, since any other compound of Formula I can be substituted into the pharmaceutical composition examples.

Pharmaceutical Dosage Form Examples

EXAMPLE A

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound of the Formula I:

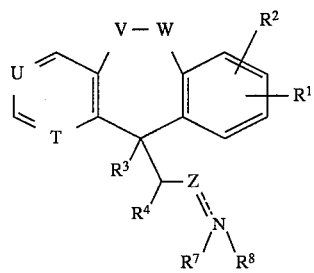 (I)

or a pharmaceutically acceptable salt or solvate thereof, wherein:

T and U each represents =CH—;

one of V and W represents oxygen and the other represents —CH$_2$—; or each of V and W represents —CH$_2$—;

R$^1$ and R$^2$ are each independently selected from the group consisting of H and halogen;

R$^3$ is alkyl, alkenyl, alkynyl, aryl, alkaryl, aralkyl, cycloalkyl, acyloxymethyl, alkoxy, alkoxymethyl, or alkyl substituted with cycloalkyl;

R$^4$ is H, alkyl, alkenyl, alkoxy, or —OH;

Z- - - - -N represents an optional double bond; when Z - - - - -N is a double bond, Z represents —CH=, or —CH$_2$C(R$^5$)=, wherein R$^5$ is H or lower alkyl; and R$^7$ and R$^8$ together represent OR$^9$;

when Z- - - - -N represents a single bond, Z represents a direct bond, —CH$_2$—, —CH=CH—, or —CH$_2$C(R$^5$)(R$^6$)—, wherein R$^5$ and R$^6$ are independently H or lower alkyl (provided that, when R$^3$ is —CH$_3$, Z is not —(CH$_2$)$_2$—); and R$^7$ and R$^8$ are independently H, alkyl, alkenyl, alkynyl, aryl, alkaryl, aralkyl, cycloalkyl, —OR$^9$; —C(O)OR$^{10}$; —CH$_2$C(O)OR$^9$; —C(O)R$^{10}$; —SO$_2$R$^{10}$; —CO-4-pyridyl-N-oxide; —(CH$_2$)$_n$—N(CH$_3$)$_2$, where n is 2 to 4; or —(CH$_2$)$_m$O(CH$_2$)$_j$OH, where m and j are independently 2 or 3;

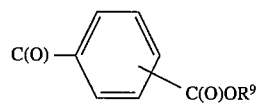

R$^9$ is H or lower alkyl; and

R$^{10}$ is alkyl or aryl.

2. A compound according to claim 1, wherein R$^3$ is alkoxy.

3. A compound according to claim 2, wherein R$^3$ is ethoxy.

4. A compound according to claim 3, wherein R$^7$ and R$^8$ are independently H, alkyl, alkenyl, alkynyl, aryl, alkaryl, or aralkyl.

5. A compound according to claim 4 having the following structure:

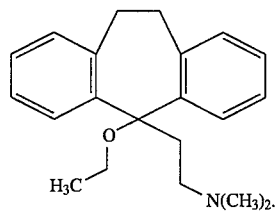

6. A compound according to claim 4 having the following structure:

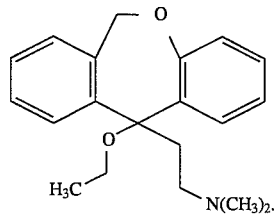

7. A compound according to claim 1, wherein R$^3$ is alkyl.

8. A compound according to claim 7, wherein R$^3$ is alkyl having from two to six carbon atoms.

9. A compound according to claim 8, wherein R$^3$ is propyl.

10. A compound according to claim 9, wherein R$^7$ and R$^8$ are independently H, alkyl, alkenyl, alkynyl, aryl, alkaryl, or aralkyl.

11. A compound according to claim 10 having the following structure:

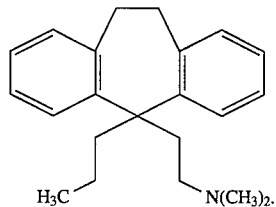

12. A compound according to claim 10 having the following structure:

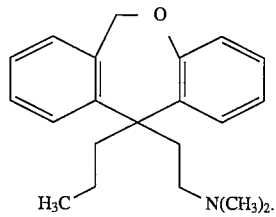

13. A compound according to claim 1, wherein R$^3$ is allyl.

14. A compound according to claim 13, wherein R$^7$ and R$^8$ are independently H, alkyl, alkenyl, alkynyl, aryl, alkaryl, or aralkyl.

15. A compound according to claim 14 having the following structure:

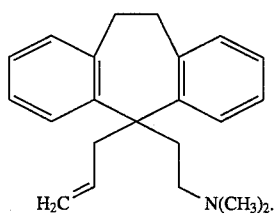

16. A compound according to claim 1, wherein $R^3$ is cyclopropylmethyl.

17. A compound according to claim 16 having the following structure:

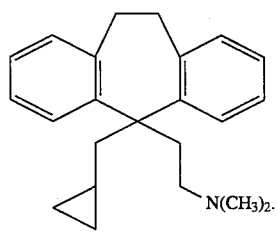

18. A compound according to claim 1, wherein $R^3$ is alkoxy, Z-----N represents a single bond, and Z is —CH$_2$—.

19. A compound according to claim 1, wherein $R^3$ is alkyl, Z-----N represents a single bond, and Z is —CH$_2$—.

20. A compound according to claim 1, wherein $R^3$ is allyl, Z-----N represents a single bond, and Z is —CH$_2$—.

21. A compound according to claim 1, wherein each of T and U represents =CH—.

22. A pharmaceutical composition comprising an effective amount of a compound of claim 1 in combination with a pharmaceutically acceptable carrier.

23. A pharmaceutical composition comprising an effective amount of a compound of the following structure IA in combination with a pharmaceutically acceptable carrier:

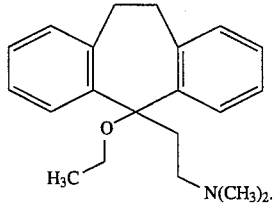
(IA)

24. A compound according to claim 1 having a structure selected from the group of structures consisting of:

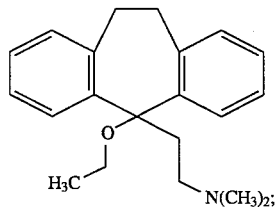
(IA)

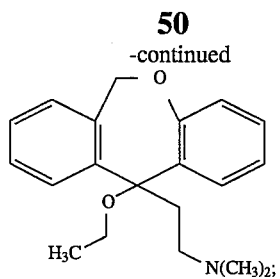
(IB)

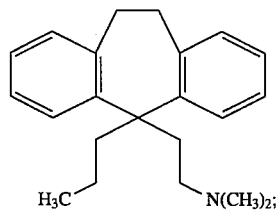
(IC)

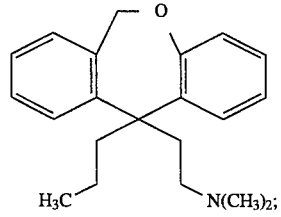
(ID)

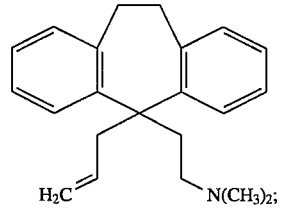
(IE)

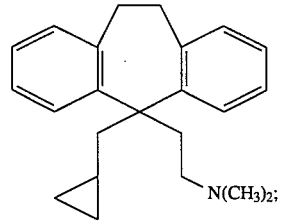
(IF)

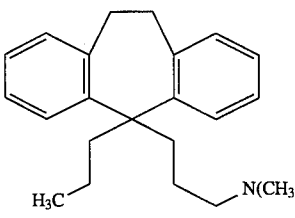
(IG)

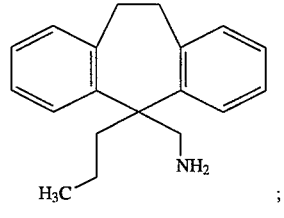
(IH)

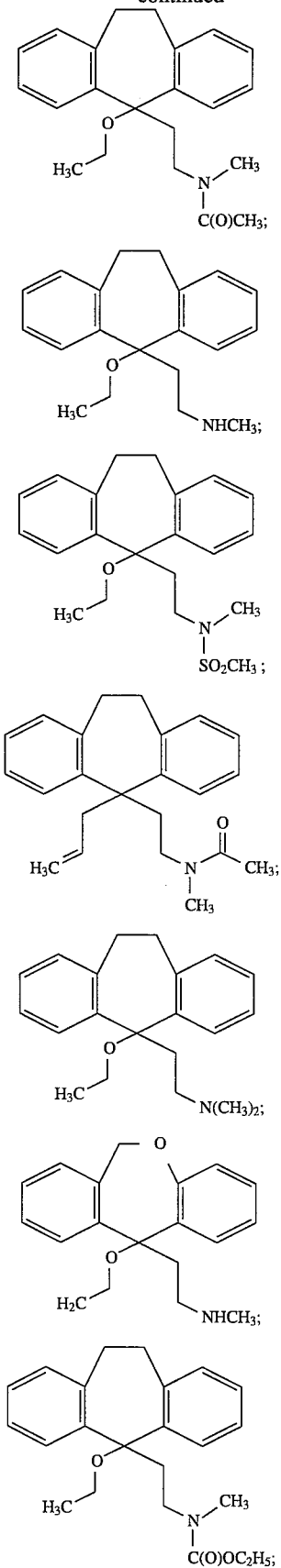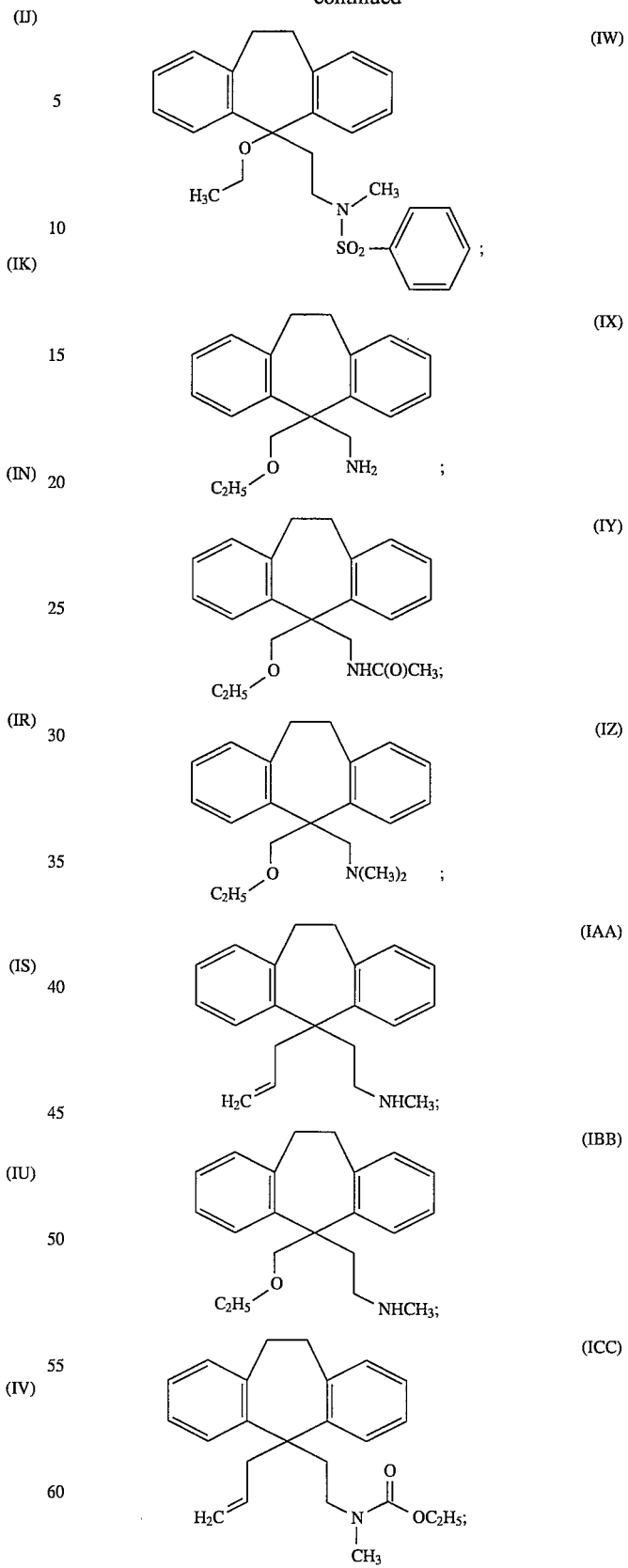

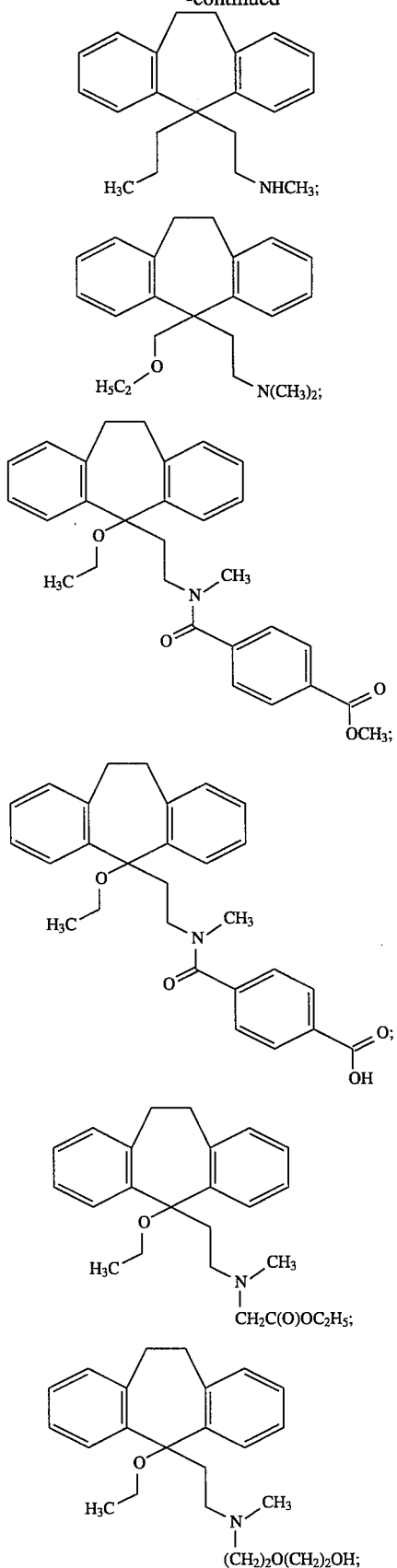
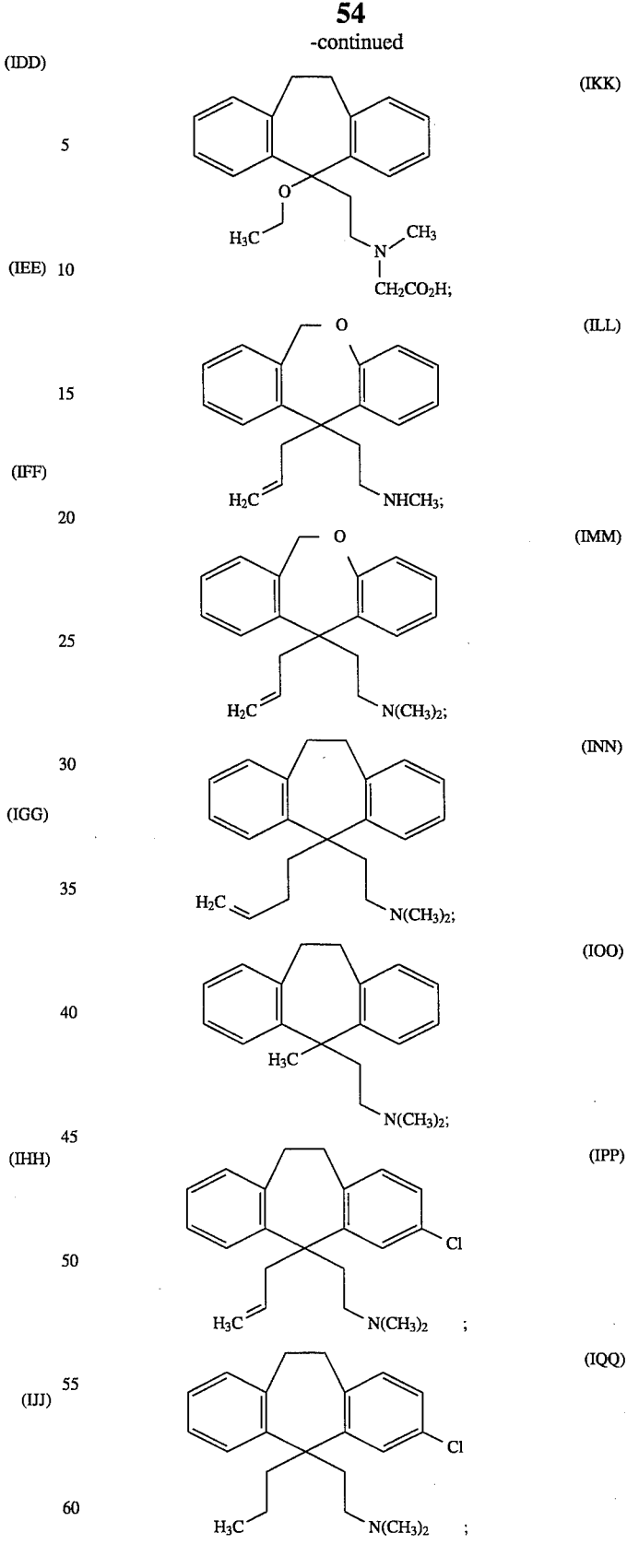

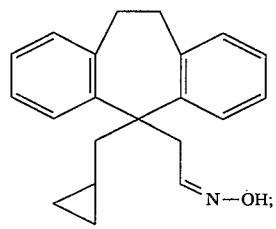
(IRR)
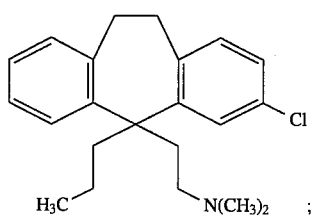
(ISS)
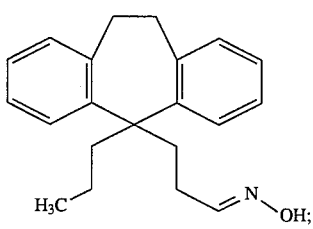
(ITT)
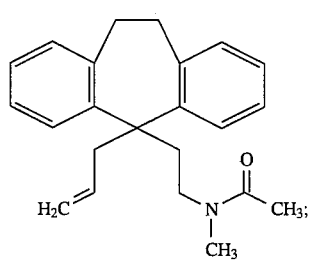
(IUU)
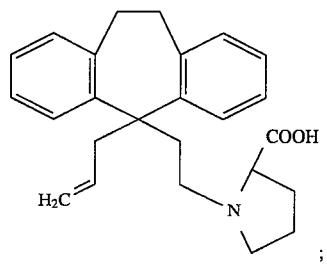
(IVV)
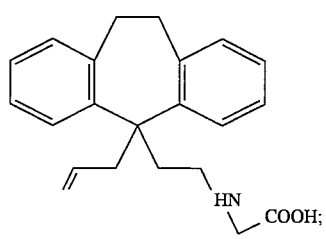
(IWW)
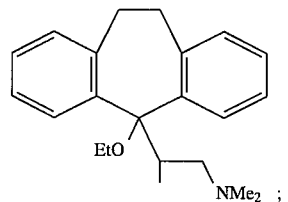
IXX
and
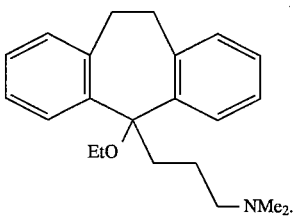
(IYY)
* * * * *